United States Patent
Bottari

(10) Patent No.: US 9,182,401 B2
(45) Date of Patent: Nov. 10, 2015

(54) USE OF THE IRAP PROTEIN FOR IMPLEMENTING METHODS OF DIAGNOSIS AND OF PROGNOSIS

(75) Inventor: Serge Bottari, Biviers (FR)

(73) Assignee: UNIVERSITE JOSEPH FOURIER, Grenoble (FR)

( * ) Notice: Subject to any disclaimer, the term of this patent is extended or adjusted under 35 U.S.C. 154(b) by 612 days.

(21) Appl. No.: 13/002,170

(22) PCT Filed: Jul. 6, 2009

(86) PCT No.: PCT/FR2009/051335
§ 371 (c)(1),
(2), (4) Date: Mar. 25, 2011

(87) PCT Pub. No.: WO2010/001079
PCT Pub. Date: Jan. 7, 2010

(65) Prior Publication Data
US 2011/0201021 A1 Aug. 18, 2011

(30) Foreign Application Priority Data
Jul. 4, 2008 (FR) ..................... 08 03802

(51) Int. Cl.
*G01N 33/573* (2006.01)
*C07K 16/40* (2006.01)
*G01N 33/574* (2006.01)
*G01N 33/68* (2006.01)

(52) U.S. Cl.
CPC .............. *G01N 33/574* (2013.01); *C07K 16/40* (2013.01); *G01N 33/689* (2013.01); *G01N 2333/471* (2013.01); *G01N 2333/96494* (2013.01); *G01N 2800/368* (2013.01)

(58) Field of Classification Search
None
See application file for complete search history.

(56) References Cited

U.S. PATENT DOCUMENTS

| 4,392,904 A | 7/1983 | Van Pelt |
| 4,474,892 A * | 10/1984 | Murad et al. ................. 436/513 |
| 2007/0020705 A1 * | 1/2007 | Mizutani ..................... 435/7.23 |

FOREIGN PATENT DOCUMENTS

WO    2005038462 A1    4/2005

OTHER PUBLICATIONS

International Preliminary Report on Patentability issued for PCT/FR2009/051335 on Mar. 1, 2011.*
Nagamatsu et al., "Determination of leukocyte elastase concentration in plasma and serum by a simple method using a specific synthetic substrate," Haemostasis, 1991, vol. 21, pp. 338-345.*
A print-out retrieved from http://www.ncbi.nlm.nih.gov/gene/4012 on Feb. 25, 2015.*
Yamahara et al.: "Placental leucine aminopeptidas/oxytocinase in maternal serum and placental during normal pregnancy", Life Science, vol. 66, No. 15, 2000, pp. 1401-1410, Cited in Specification, French Search Report and ISR.
Tsujimoto et al.: "The Oxytocinase subfamily of M1 aminopeptidases", Biochimica ET Biophysica Acta (BBA)—Proteins & Proteomics, Elsevier, vol. 1751, No. 1, Aug. 1, 2005, pp. 9-18, Cited in Specification, French Search Report and ISR.
Albiston et al.: "Therapeutic targeting of insulin-regulated aminopeptidase: Heads and tails?" Pharmacology and Therapeutics, Elsevier, GB, vol. 116, No. 3, Nov. 20, 2007, pp. 417-427, Cited in Specification, French Search Report and ISR.
Iwase et al.: "Characterization of a secretase activity for placental leucine aminopeptidase" Archives of Biochemistry and Biophysics, vol. 393, No. 1, Aug. 10, 2001, pp. 163-169, Cited in Specification, French Search Report and ISR.
International Search Report, dated Dec. 1, 2009, from corresponding PCT application.
French Search Report, dated Jan. 29, 2009, from corresponding French application.

* cited by examiner

*Primary Examiner* — Galina Yakovleva
(74) *Attorney, Agent, or Firm* — Young & Thompson

(57) ABSTRACT

The use of the IRAP protein for implementing methods of diagnosis and of prognosis.

5 Claims, 2 Drawing Sheets

SEQUENCE LISTING

```
<160> NUMBER OF SEQ ID NOS: 11

<210> SEQ ID NO 1
<211> LENGTH: 1025
<212> TYPE: PRT
<213> ORGANISM: Homo sapiens
<220> FEATURE:
<221> NAME/KEY: PEPTIDE
<222> LOCATION: (1)..(1025)

<400> SEQUENCE: 1

Met Glu Pro Phe Thr Asn Asp Arg Leu Gln Leu Pro Arg Asn Met Ile
1               5                   10                  15

Glu Asn Ser Met Phe Glu Glu Glu Pro Asp Val Val Asp Leu Ala Lys
```

```
                20                  25                  30
Glu Pro Cys Leu His Pro Leu Glu Pro Asp Glu Val Glu Tyr Glu Pro
             35                  40                  45

Arg Gly Ser Arg Leu Leu Val Arg Gly Leu Gly Glu His Glu Met Glu
 50                  55                  60

Glu Asp Glu Asp Tyr Glu Ser Ser Ala Lys Leu Leu Gly Met Ser
 65                  70                  75                  80

Phe Met Asn Arg Ser Gly Leu Arg Asn Ser Ala Thr Gly Tyr Arg
                 85                  90                  95

Gln Ser Pro Asp Gly Ala Cys Ser Val Pro Ser Ala Arg Thr Met Val
                100                 105                 110

Val Cys Ala Phe Val Ile Val Ala Val Ser Val Ile Met Val Ile
            115                 120                 125

Tyr Leu Leu Pro Arg Cys Thr Phe Thr Lys Glu Gly Cys His Lys Lys
            130                 135                 140

Asn Gln Ser Ile Gly Leu Ile Gln Pro Phe Ala Thr Asn Gly Lys Leu
145                 150                 155                 160

Phe Pro Trp Ala Gln Ile Arg Leu Pro Thr Ala Val Val Pro Leu Arg
                165                 170                 175

Tyr Glu Leu Ser Leu His Pro Asn Leu Thr Ser Met Thr Phe Arg Gly
                180                 185                 190

Ser Val Thr Ile Ser Val Gln Ala Leu Gln Val Thr Trp Asn Ile Ile
            195                 200                 205

Leu His Ser Thr Gly His Asn Ile Ser Arg Val Thr Phe Met Ser Ala
            210                 215                 220

Val Ser Ser Gln Glu Lys Gln Ala Glu Ile Leu Glu Tyr Ala Tyr His
225                 230                 235                 240

Gly Gln Ile Ala Ile Val Ala Pro Glu Ala Leu Leu Ala Gly His Asn
                245                 250                 255

Tyr Thr Leu Lys Ile Glu Tyr Ser Ala Asn Ile Ser Ser Tyr Tyr
                260                 265                 270

Gly Phe Tyr Gly Phe Ser Tyr Thr Asp Glu Ser Asn Glu Lys Lys Tyr
            275                 280                 285

Phe Ala Ala Thr Gln Phe Glu Pro Leu Ala Ala Arg Ser Ala Phe Pro
290                 295                 300

Cys Phe Asp Glu Pro Ala Phe Lys Ala Thr Phe Ile Ile Lys Ile Ile
305                 310                 315                 320

Arg Asp Glu Gln Tyr Thr Ala Leu Ser Asn Met Pro Lys Lys Ser
                325                 330                 335

Val Val Leu Asp Asp Gly Leu Val Gln Asp Glu Phe Ser Glu Ser Val
            340                 345                 350

Lys Met Ser Thr Tyr Leu Val Ala Phe Ile Val Gly Glu Met Lys Asn
            355                 360                 365

Leu Ser Gln Asp Val Asn Gly Thr Leu Val Ser Ile Tyr Ala Val Pro
    370                 375                 380

Glu Lys Ile Gly Gln Val His Tyr Ala Leu Glu Thr Thr Val Lys Leu
385                 390                 395                 400

Leu Glu Phe Phe Gln Asn Tyr Phe Glu Ile Gln Tyr Pro Leu Lys Lys
                405                 410                 415

Leu Asp Leu Val Ala Ile Pro Asp Phe Glu Ala Gly Ala Met Glu Asn
                420                 425                 430

Trp Gly Leu Leu Thr Phe Arg Glu Glu Thr Leu Leu Tyr Asp Ser Asn
            435                 440                 445
```

```
Thr Ser Ser Met Ala Asp Arg Lys Leu Val Thr Lys Ile Ile Ala His
    450                 455                 460

Glu Leu Ala His Gln Trp Phe Gly Asn Leu Val Thr Met Lys Trp Trp
465                 470                 475                 480

Asn Asp Leu Trp Leu Asn Glu Gly Phe Ala Thr Phe Met Glu Tyr Phe
                485                 490                 495

Ser Leu Glu Lys Ile Phe Lys Glu Leu Ser Ser Tyr Glu Asp Phe Leu
            500                 505                 510

Asp Ala Arg Phe Lys Thr Met Lys Lys Asp Ser Leu Asn Ser Ser His
        515                 520                 525

Pro Ile Ser Ser Ser Val Gln Ser Ser Glu Gln Ile Glu Glu Met Phe
    530                 535                 540

Asp Ser Leu Ser Tyr Phe Lys Gly Ser Ser Leu Leu Leu Met Leu Lys
545                 550                 555                 560

Thr Tyr Leu Ser Glu Asp Val Phe Gln His Ala Val Val Leu Tyr Leu
                565                 570                 575

His Asn His Ser Tyr Ala Ser Ile Gln Ser Asp Asp Leu Trp Asp Ser
            580                 585                 590

Phe Asn Glu Val Thr Asn Gln Thr Leu Asp Val Lys Arg Met Met Lys
        595                 600                 605

Thr Trp Thr Leu Gln Lys Gly Phe Pro Leu Val Thr Val Gln Lys Lys
    610                 615                 620

Gly Lys Glu Leu Phe Ile Gln Gln Glu Arg Phe Phe Leu Asn Met Lys
625                 630                 635                 640

Pro Glu Ile Gln Pro Ser Asp Thr Ser Tyr Leu Trp His Ile Pro Leu
                645                 650                 655

Ser Tyr Val Thr Glu Gly Arg Asn Tyr Ser Lys Tyr Gln Ser Val Ser
            660                 665                 670

Leu Leu Asp Lys Lys Ser Gly Val Ile Asn Leu Thr Glu Glu Val Leu
        675                 680                 685

Trp Val Lys Val Asn Ile Asn Met Asn Gly Tyr Tyr Ile Val His Tyr
    690                 695                 700

Ala Asp Asp Asp Trp Glu Ala Leu Ile His Gln Leu Lys Ile Asn Pro
705                 710                 715                 720

Tyr Val Leu Ser Asp Lys Asp Arg Ala Asn Leu Ile Asn Asn Ile Phe
                725                 730                 735

Glu Leu Ala Gly Leu Gly Lys Val Pro Leu Lys Arg Ala Phe Asp Leu
            740                 745                 750

Ile Asn Tyr Leu Gly Asn Glu Asn His Thr Ala Pro Ile Thr Glu Ala
        755                 760                 765

Leu Phe Gln Thr Asp Leu Ile Tyr Asn Leu Leu Glu Lys Leu Gly Tyr
    770                 775                 780

Met Asp Leu Ala Ser Arg Leu Val Thr Arg Val Phe Lys Leu Leu Gln
785                 790                 795                 800

Asn Gln Ile Gln Gln Thr Trp Thr Asp Glu Gly Thr Pro Ser Met
                805                 810                 815

Arg Glu Leu Arg Ser Ala Leu Leu Glu Phe Ala Cys Thr His Asn Leu
            820                 825                 830

Gly Asn Cys Ser Thr Thr Ala Met Lys Leu Phe Asp Asp Trp Met Ala
        835                 840                 845

Ser Asn Gly Thr Gln Ser Leu Pro Thr Asp Val Met Thr Thr Val Phe
    850                 855                 860
```

```
Lys Val Gly Ala Lys Thr Asp Lys Gly Trp Ser Phe Leu Leu Gly Lys
865                 870                 875                 880

Tyr Ile Ser Ile Gly Ser Glu Ala Glu Lys Asn Lys Ile Leu Glu Ala
                885                 890                 895

Leu Ala Ser Ser Glu Asp Val Arg Lys Leu Tyr Trp Leu Met Lys Ser
            900                 905                 910

Ser Leu Asn Gly Asp Asn Phe Arg Thr Gln Lys Leu Ser Phe Ile Ile
        915                 920                 925

Arg Thr Val Gly Arg His Phe Pro Gly His Leu Leu Ala Trp Asp Phe
    930                 935                 940

Val Lys Glu Asn Trp Asn Lys Leu Val Gln Lys Phe Pro Leu Gly Ser
945                 950                 955                 960

Tyr Thr Ile Gln Asn Ile Val Ala Gly Ser Thr Tyr Leu Phe Ser Thr
                965                 970                 975

Lys Thr His Leu Ser Glu Val Gln Ala Phe Phe Glu Asn Gln Ser Glu
            980                 985                 990

Ala Thr Phe Arg Leu Arg Cys Val Gln Glu Ala Leu Glu Val Ile Gln
        995                 1000                1005

Leu Asn Ile Gln Trp Met Glu Lys Asn Leu Lys Ser Leu Thr Trp
    1010                1015                1020

Trp Leu
    1025

<210> SEQ ID NO 2
<211> LENGTH: 1011
<212> TYPE: PRT
<213> ORGANISM: Homo sapiens
<220> FEATURE:
<221> NAME/KEY: PEPTIDE
<222> LOCATION: (1)..(1011)

<400> SEQUENCE: 2

Met Ile Glu Asn Ser Met Phe Glu Glu Pro Asp Val Val Asp Leu
1               5                   10                  15

Ala Lys Glu Pro Cys Leu His Pro Leu Glu Pro Asp Glu Val Glu Tyr
            20                  25                  30

Glu Pro Arg Gly Ser Arg Leu Leu Val Arg Gly Leu Gly Glu His Glu
        35                  40                  45

Met Glu Glu Asp Glu Asp Tyr Glu Ser Ser Ala Lys Leu Leu Gly
    50                  55                  60

Met Ser Phe Met Asn Arg Ser Ser Gly Leu Arg Asn Ser Ala Thr Gly
65                  70                  75                  80

Tyr Arg Gln Ser Pro Asp Gly Ala Cys Ser Val Pro Ser Ala Arg Thr
                85                  90                  95

Met Val Val Cys Ala Phe Val Ile Val Ala Val Ser Val Ile Met
            100                 105                 110

Val Ile Tyr Leu Leu Pro Arg Cys Thr Phe Thr Lys Glu Gly Cys His
        115                 120                 125

Lys Lys Asn Gln Ser Ile Gly Leu Ile Gln Pro Phe Ala Thr Asn Gly
    130                 135                 140

Lys Leu Phe Pro Trp Ala Gln Ile Arg Leu Pro Thr Ala Val Val Pro
145                 150                 155                 160

Leu Arg Tyr Glu Leu Ser Leu His Pro Asn Leu Thr Ser Met Thr Phe
                165                 170                 175

Arg Gly Ser Val Thr Ile Ser Val Gln Ala Leu Gln Val Thr Trp Asn
            180                 185                 190
```

```
Ile Ile Leu His Ser Thr Gly His Asn Ile Ser Arg Val Thr Phe Met
            195                 200                 205
Ser Ala Val Ser Ser Gln Glu Lys Gln Ala Glu Ile Leu Glu Tyr Ala
210                 215                 220
Tyr His Gly Gln Ile Ala Ile Val Ala Pro Glu Ala Leu Leu Ala Gly
225                 230                 235                 240
His Asn Tyr Thr Leu Lys Ile Glu Tyr Ser Ala Asn Ile Ser Ser Ser
            245                 250                 255
Tyr Tyr Gly Phe Tyr Gly Phe Ser Tyr Thr Asp Ser Asn Glu Lys
                260                 265                 270
Lys Tyr Phe Ala Ala Thr Gln Phe Glu Pro Leu Ala Ala Arg Ser Ala
            275                 280                 285
Phe Pro Cys Phe Asp Glu Pro Ala Phe Lys Ala Thr Phe Ile Ile Lys
            290                 295                 300
Ile Ile Arg Asp Glu Gln Tyr Thr Ala Leu Ser Asn Met Pro Lys Lys
305                 310                 315                 320
Ser Ser Val Val Leu Asp Asp Gly Leu Val Gln Asp Glu Phe Ser Glu
                325                 330                 335
Ser Val Lys Met Ser Thr Tyr Leu Val Ala Phe Ile Val Gly Glu Met
            340                 345                 350
Lys Asn Leu Ser Gln Asp Val Asn Gly Thr Leu Val Ser Ile Tyr Ala
            355                 360                 365
Val Pro Glu Lys Ile Gly Gln Val His Tyr Ala Leu Glu Thr Thr Val
            370                 375                 380
Lys Leu Leu Glu Phe Phe Gln Asn Tyr Phe Glu Ile Gln Tyr Pro Leu
385                 390                 395                 400
Lys Lys Leu Asp Leu Val Ala Ile Pro Asp Phe Glu Ala Gly Ala Met
                405                 410                 415
Glu Asn Trp Gly Leu Leu Thr Phe Arg Glu Glu Thr Leu Leu Tyr Asp
                420                 425                 430
Ser Asn Thr Ser Ser Met Ala Asp Arg Lys Leu Val Thr Lys Ile Ile
            435                 440                 445
Ala His Glu Leu Ala His Gln Trp Phe Gly Asn Leu Val Thr Met Lys
            450                 455                 460
Trp Trp Asn Asp Leu Trp Leu Asn Glu Gly Phe Ala Thr Phe Met Glu
465                 470                 475                 480
Tyr Phe Ser Leu Glu Lys Ile Phe Lys Glu Leu Ser Ser Tyr Glu Asp
                485                 490                 495
Phe Leu Asp Ala Arg Phe Lys Thr Met Lys Lys Asp Ser Leu Asn Ser
                500                 505                 510
Ser His Pro Ile Ser Ser Val Gln Ser Ser Glu Gln Ile Glu Glu
            515                 520                 525
Met Phe Asp Ser Leu Ser Tyr Phe Lys Gly Ser Ser Leu Leu Met
            530                 535                 540
Leu Lys Thr Tyr Leu Ser Glu Asp Val Phe Gln His Ala Val Val Leu
545                 550                 555                 560
Tyr Leu His Asn His Ser Tyr Ala Ser Ile Gln Ser Asp Leu Trp
                565                 570                 575
Asp Ser Phe Asn Glu Val Thr Asn Gln Thr Leu Asp Val Lys Arg Met
                580                 585                 590
Met Lys Thr Trp Thr Leu Gln Lys Gly Phe Pro Leu Val Thr Val Gln
            595                 600                 605
```

```
Lys Lys Gly Lys Glu Leu Phe Ile Gln Gln Glu Arg Phe Phe Leu Asn
            610                 615                 620

Met Lys Pro Glu Ile Gln Pro Ser Asp Thr Ser Tyr Leu Trp His Ile
625                 630                 635                 640

Pro Leu Ser Tyr Val Thr Glu Gly Arg Asn Tyr Ser Lys Tyr Gln Ser
                645                 650                 655

Val Ser Leu Leu Asp Lys Lys Ser Gly Val Ile Asn Leu Thr Glu Glu
            660                 665                 670

Val Leu Trp Val Lys Val Asn Ile Asn Met Asn Gly Tyr Tyr Ile Val
            675                 680                 685

His Tyr Ala Asp Asp Asp Trp Glu Ala Leu Ile His Gln Leu Lys Ile
690                 695                 700

Asn Pro Tyr Val Leu Ser Asp Lys Asp Arg Ala Asn Leu Ile Asn Asn
705                 710                 715                 720

Ile Phe Glu Leu Ala Gly Leu Gly Lys Val Pro Leu Lys Arg Ala Phe
                725                 730                 735

Asp Leu Ile Asn Tyr Leu Gly Asn Glu Asn His Thr Ala Pro Ile Thr
            740                 745                 750

Glu Ala Leu Phe Gln Thr Asp Leu Ile Tyr Asn Leu Leu Glu Lys Leu
            755                 760                 765

Gly Tyr Met Asp Leu Ala Ser Arg Leu Val Thr Arg Val Phe Lys Leu
770                 775                 780

Leu Gln Asn Gln Ile Gln Gln Gln Thr Trp Thr Asp Glu Gly Thr Pro
785                 790                 795                 800

Ser Met Arg Glu Leu Arg Ser Ala Leu Leu Glu Phe Ala Cys Thr His
                805                 810                 815

Asn Leu Gly Asn Cys Ser Thr Thr Ala Met Lys Leu Phe Asp Asp Trp
            820                 825                 830

Met Ala Ser Asn Gly Thr Gln Ser Leu Pro Thr Asp Val Met Thr Thr
835                 840                 845

Val Phe Lys Val Gly Ala Lys Thr Asp Lys Gly Trp Ser Phe Leu Leu
850                 855                 860

Gly Lys Tyr Ile Ser Ile Gly Ser Glu Ala Glu Lys Asn Lys Ile Leu
865                 870                 875                 880

Glu Ala Leu Ala Ser Ser Glu Asp Val Arg Lys Leu Tyr Trp Leu Met
                885                 890                 895

Lys Ser Ser Leu Asn Gly Asp Asn Phe Arg Thr Gln Lys Leu Ser Phe
            900                 905                 910

Ile Ile Arg Thr Val Gly Arg His Phe Pro Gly His Leu Leu Ala Trp
            915                 920                 925

Asp Phe Val Lys Glu Asn Trp Asn Lys Leu Val Gln Lys Phe Pro Leu
930                 935                 940

Gly Ser Tyr Thr Ile Gln Asn Ile Val Ala Gly Ser Thr Tyr Leu Phe
945                 950                 955                 960

Ser Thr Lys Thr His Leu Ser Glu Val Gln Ala Phe Phe Glu Asn Gln
                965                 970                 975

Ser Glu Ala Thr Phe Arg Leu Arg Cys Val Gln Glu Ala Leu Glu Val
            980                 985                 990

Ile Gln Leu Asn Ile Gln Trp Met Glu Lys Asn Leu Lys Ser Leu Thr
            995                 1000                1005

Trp Trp Leu
    1010
```

-continued

```
<210> SEQ ID NO 3
<211> LENGTH: 1006
<212> TYPE: PRT
<213> ORGANISM: Homo sapiens
<220> FEATURE:
<221> NAME/KEY: PEPTIDE
<222> LOCATION: (1)..(1006)

<400> SEQUENCE: 3

Met Phe Glu Glu Glu Pro Asp Val Val Asp Leu Ala Lys Glu Pro Cys
1               5                   10                  15

Leu His Pro Leu Glu Pro Asp Glu Val Glu Tyr Glu Pro Arg Gly Ser
            20                  25                  30

Arg Leu Leu Val Arg Gly Leu Gly Glu His Glu Met Glu Glu Asp Glu
        35                  40                  45

Glu Asp Tyr Glu Ser Ser Ala Lys Leu Leu Gly Met Ser Phe Met Asn
    50                  55                  60

Arg Ser Ser Gly Leu Arg Asn Ser Ala Thr Gly Tyr Arg Gln Ser Pro
65                  70                  75                  80

Asp Gly Ala Cys Ser Val Pro Ser Ala Arg Thr Met Val Val Cys Ala
                85                  90                  95

Phe Val Ile Val Ala Val Ser Val Ile Met Val Ile Tyr Leu Leu
            100                 105                 110

Pro Arg Cys Thr Phe Thr Lys Glu Gly Cys His Lys Lys Asn Gln Ser
        115                 120                 125

Ile Gly Leu Ile Gln Pro Phe Ala Thr Asn Gly Lys Leu Phe Pro Trp
    130                 135                 140

Ala Gln Ile Arg Leu Pro Thr Ala Val Val Pro Leu Arg Tyr Glu Leu
145                 150                 155                 160

Ser Leu His Pro Asn Leu Thr Ser Met Thr Phe Arg Gly Ser Val Thr
                165                 170                 175

Ile Ser Val Gln Ala Leu Gln Val Thr Trp Asn Ile Ile Leu His Ser
            180                 185                 190

Thr Gly His Asn Ile Ser Arg Val Thr Phe Met Ser Ala Val Ser Ser
        195                 200                 205

Gln Glu Lys Gln Ala Glu Ile Leu Glu Tyr Ala Tyr His Gly Gln Ile
    210                 215                 220

Ala Ile Val Ala Pro Glu Ala Leu Leu Ala Gly His Asn Tyr Thr Leu
225                 230                 235                 240

Lys Ile Glu Tyr Ser Ala Asn Ile Ser Ser Ser Tyr Gly Phe Tyr
                245                 250                 255

Gly Phe Ser Tyr Thr Asp Glu Ser Asn Glu Lys Lys Tyr Phe Ala Ala
            260                 265                 270

Thr Gln Phe Glu Pro Leu Ala Ala Arg Ser Ala Phe Pro Cys Phe Asp
        275                 280                 285

Glu Pro Ala Phe Lys Ala Thr Phe Ile Ile Lys Ile Arg Asp Glu
    290                 295                 300

Gln Tyr Thr Ala Leu Ser Asn Met Pro Lys Lys Ser Ser Val Val Leu
305                 310                 315                 320

Asp Asp Gly Leu Val Gln Asp Glu Phe Ser Glu Ser Val Lys Met Ser
                325                 330                 335

Thr Tyr Leu Val Ala Phe Ile Val Gly Glu Met Lys Asn Leu Ser Gln
            340                 345                 350

Asp Val Asn Gly Thr Leu Val Ser Ile Tyr Ala Val Pro Glu Lys Ile
        355                 360                 365
```

-continued

Gly Gln Val His Tyr Ala Leu Glu Thr Thr Val Lys Leu Leu Glu Phe
    370             375             380

Phe Gln Asn Tyr Phe Glu Ile Gln Tyr Pro Leu Lys Lys Leu Asp Leu
385             390             395             400

Val Ala Ile Pro Asp Phe Glu Ala Gly Ala Met Glu Asn Trp Gly Leu
            405             410             415

Leu Thr Phe Arg Glu Glu Thr Leu Leu Tyr Asp Ser Asn Thr Ser Ser
            420             425             430

Met Ala Asp Arg Lys Leu Val Thr Lys Ile Ile Ala His Glu Leu Ala
            435             440             445

His Gln Trp Phe Gly Asn Leu Val Thr Met Lys Trp Trp Asn Asp Leu
    450             455             460

Trp Leu Asn Glu Gly Phe Ala Thr Phe Met Glu Tyr Phe Ser Leu Glu
465             470             475             480

Lys Ile Phe Lys Glu Leu Ser Ser Tyr Glu Asp Phe Leu Asp Ala Arg
            485             490             495

Phe Lys Thr Met Lys Lys Asp Ser Leu Asn Ser Ser His Pro Ile Ser
            500             505             510

Ser Ser Val Gln Ser Ser Glu Gln Ile Glu Glu Met Phe Asp Ser Leu
            515             520             525

Ser Tyr Phe Lys Gly Ser Ser Leu Leu Leu Met Leu Lys Thr Tyr Leu
    530             535             540

Ser Glu Asp Val Phe Gln His Ala Val Val Leu Tyr Leu His Asn His
545             550             555             560

Ser Tyr Ala Ser Ile Gln Ser Asp Asp Leu Trp Asp Ser Phe Asn Glu
            565             570             575

Val Thr Asn Gln Thr Leu Asp Val Lys Arg Met Met Lys Thr Trp Thr
            580             585             590

Leu Gln Lys Gly Phe Pro Leu Val Thr Val Gln Lys Lys Gly Lys Glu
            595             600             605

Leu Phe Ile Gln Gln Glu Arg Phe Phe Leu Asn Met Lys Pro Glu Ile
    610             615             620

Gln Pro Ser Asp Thr Ser Tyr Leu Trp His Ile Pro Leu Ser Tyr Val
625             630             635             640

Thr Glu Gly Arg Asn Tyr Ser Lys Tyr Gln Ser Val Ser Leu Leu Asp
            645             650             655

Lys Lys Ser Gly Val Ile Asn Leu Thr Glu Glu Val Leu Trp Val Lys
            660             665             670

Val Asn Ile Asn Met Asn Gly Tyr Tyr Ile Val His Tyr Ala Asp Asp
            675             680             685

Asp Trp Glu Ala Leu Ile His Gln Leu Lys Ile Asn Pro Tyr Val Leu
    690             695             700

Ser Asp Lys Asp Arg Ala Asn Leu Ile Asn Asn Ile Phe Glu Leu Ala
705             710             715             720

Gly Leu Gly Lys Val Pro Leu Lys Arg Ala Phe Asp Leu Ile Asn Tyr
            725             730             735

Leu Gly Asn Glu Asn His Thr Ala Pro Ile Thr Glu Ala Leu Phe Gln
            740             745             750

Thr Asp Leu Ile Tyr Asn Leu Leu Glu Lys Leu Gly Tyr Met Asp Leu
            755             760             765

Ala Ser Arg Leu Val Thr Arg Val Phe Lys Leu Leu Gln Asn Gln Ile
    770             775             780

Gln Gln Gln Thr Trp Thr Asp Glu Gly Thr Pro Ser Met Arg Glu Leu

```
                785                 790                 795                 800
Arg Ser Ala Leu Leu Glu Phe Ala Cys Thr His Asn Leu Gly Asn Cys
                805                 810                 815

Ser Thr Thr Ala Met Lys Leu Phe Asp Asp Trp Met Ala Ser Asn Gly
            820                 825                 830

Thr Gln Ser Leu Pro Thr Asp Val Met Thr Thr Val Phe Lys Val Gly
            835                 840                 845

Ala Lys Thr Asp Lys Gly Trp Ser Phe Leu Leu Gly Lys Tyr Ile Ser
        850                 855                 860

Ile Gly Ser Glu Ala Glu Lys Asn Lys Ile Leu Glu Ala Leu Ala Ser
865                 870                 875                 880

Ser Glu Asp Val Arg Lys Leu Tyr Trp Leu Met Lys Ser Ser Leu Asn
                885                 890                 895

Gly Asp Asn Phe Arg Thr Gln Lys Leu Ser Phe Ile Ile Arg Thr Val
            900                 905                 910

Gly Arg His Phe Pro Gly His Leu Leu Ala Trp Asp Phe Val Lys Glu
        915                 920                 925

Asn Trp Asn Lys Leu Val Gln Lys Phe Pro Leu Gly Ser Tyr Thr Ile
930                 935                 940

Gln Asn Ile Val Ala Gly Ser Thr Tyr Leu Phe Ser Thr Lys Thr His
945                 950                 955                 960

Leu Ser Glu Val Gln Ala Phe Phe Glu Asn Gln Ser Glu Ala Thr Phe
                965                 970                 975

Arg Leu Arg Cys Val Gln Glu Ala Leu Glu Val Ile Gln Leu Asn Ile
            980                 985                 990

Gln Trp Met Glu Lys Asn Leu Lys  Ser Leu Thr Trp Trp  Leu
        995                 1000                1005

<210> SEQ ID NO 4
<211> LENGTH: 1025
<212> TYPE: PRT
<213> ORGANISM: Homo sapiens
<220> FEATURE:
<221> NAME/KEY: PEPTIDE
<222> LOCATION: (1)..(1025)

<400> SEQUENCE: 4

Met Glu Pro Phe Thr Asn Asp Arg Leu Gln Leu Pro Arg Asn Met Ile
1               5                   10                  15

Glu Asn Ser Met Phe Glu Glu Pro Asp Val Val Asp Leu Ala Lys
            20                  25                  30

Glu Pro Cys Leu His Pro Leu Glu Pro Asp Glu Val Glu Tyr Glu Pro
        35                  40                  45

Arg Gly Ser Arg Leu Leu Val Arg Gly Leu Gly Glu His Glu Met Glu
    50                  55                  60

Glu Asp Glu Glu Asp Tyr Glu Ser Ser Ala Lys Leu Leu Gly Met Ser
65                  70                  75                  80

Phe Met Asn Arg Ser Pro Gly Leu Arg Asn Ser Ala Thr Gly Tyr Arg
                85                  90                  95

Gln Ser Pro Asp Gly Ala Cys Ser Val Pro Ser Ala Arg Thr Met Val
            100                 105                 110

Val Cys Ala Phe Val Ile Val Val Ala Val Ser Val Ile Met Val Ile
        115                 120                 125

Tyr Leu Leu Pro Arg Cys Thr Phe Thr Lys Glu Gly Cys His Lys Lys
    130                 135                 140
```

```
Asn Gln Ser Ile Gly Leu Ile Gln Pro Phe Ala Thr Asn Gly Lys Leu
145                 150                 155                 160

Phe Pro Trp Ala Gln Ile Arg Leu Pro Thr Ala Val Val Pro Leu Arg
                165                 170                 175

Tyr Glu Leu Ser Leu His Pro Asn Leu Thr Ser Met Thr Phe Arg Gly
            180                 185                 190

Ser Val Thr Ile Ser Val Gln Ala Leu Gln Val Thr Trp Asn Ile Ile
        195                 200                 205

Leu His Ser Thr Gly His Asn Ile Ser Arg Val Thr Phe Met Ser Ala
    210                 215                 220

Val Ser Ser Gln Glu Lys Gln Ala Glu Ile Leu Glu Tyr Ala Tyr His
225                 230                 235                 240

Gly Gln Ile Ala Ile Val Ala Pro Glu Ala Leu Leu Ala Gly His Asn
                245                 250                 255

Tyr Thr Leu Lys Ile Glu Tyr Ser Ala Asn Ile Ser Ser Ser Tyr Tyr
            260                 265                 270

Gly Phe Tyr Gly Phe Ser Tyr Thr Asp Glu Ser Asn Glu Lys Lys Tyr
        275                 280                 285

Phe Ala Ala Thr Gln Phe Glu Pro Leu Ala Ala Arg Ser Ala Phe Pro
    290                 295                 300

Cys Phe Asp Glu Pro Ala Phe Lys Ala Thr Phe Ile Ile Lys Ile Ile
305                 310                 315                 320

Arg Asp Glu Gln Tyr Thr Ala Leu Ser Asn Met Pro Lys Lys Ser Ser
                325                 330                 335

Val Val Leu Asp Asp Gly Leu Val Gln Asp Glu Phe Ser Glu Ser Val
            340                 345                 350

Lys Met Ser Thr Tyr Leu Val Ala Phe Ile Val Gly Glu Met Lys Asn
        355                 360                 365

Leu Ser Gln Asp Val Asn Gly Thr Leu Val Ser Ile Tyr Ala Val Pro
    370                 375                 380

Glu Lys Ile Gly Gln Val His Tyr Ala Leu Glu Thr Thr Val Lys Leu
385                 390                 395                 400

Leu Glu Phe Phe Gln Asn Tyr Phe Glu Ile Gln Tyr Pro Leu Lys Lys
                405                 410                 415

Leu Asp Leu Val Ala Ile Pro Asp Phe Glu Ala Gly Ala Met Glu Asn
            420                 425                 430

Trp Gly Leu Leu Thr Phe Arg Glu Glu Thr Leu Leu Tyr Asp Ser Asn
        435                 440                 445

Thr Ser Ser Met Ala Asp Arg Lys Leu Val Thr Lys Ile Ile Ala His
    450                 455                 460

Glu Leu Ala His Gln Trp Phe Gly Asn Leu Val Thr Met Lys Trp Trp
465                 470                 475                 480

Asn Asp Leu Trp Leu Asn Glu Gly Phe Ala Thr Phe Met Glu Tyr Phe
                485                 490                 495

Ser Leu Glu Lys Ile Phe Lys Gly Leu Ser Ser Tyr Glu Asp Phe Leu
            500                 505                 510

Asp Ala Arg Phe Lys Thr Met Lys Lys Asp Ser Leu Asn Ser Ser His
        515                 520                 525

Pro Ile Ser Ser Ser Val Gln Ser Ser Glu Gln Ile Glu Glu Met Phe
    530                 535                 540

Asp Ser Leu Ser Tyr Phe Lys Gly Ser Ser Leu Leu Leu Met Leu Lys
545                 550                 555                 560

Thr Tyr Leu Ser Glu Asp Val Phe Gln His Ala Val Val Leu Tyr Leu
```

-continued

```
            565                 570                 575
His Asn His Ser Tyr Ala Ser Ile Gln Ser Asp Asp Leu Trp Asp Ser
            580                 585                 590

Phe Asn Glu Val Thr Asn Gln Thr Leu Asp Val Lys Arg Met Met Lys
            595                 600                 605

Thr Trp Thr Leu Gln Lys Gly Phe Pro Leu Val Thr Val Gln Lys Lys
            610                 615                 620

Gly Lys Glu Leu Phe Ile Gln Gln Glu Arg Phe Phe Leu Asn Met Lys
625                 630                 635                 640

Pro Glu Ile Gln Pro Ser Asp Thr Ser Tyr Leu Trp His Ile Pro Leu
            645                 650                 655

Ser Tyr Val Thr Glu Gly Arg Asn Tyr Ser Lys Tyr Gln Ser Val Ser
            660                 665                 670

Leu Leu Asp Lys Lys Ser Gly Val Ile Asn Leu Thr Glu Glu Val Leu
            675                 680                 685

Trp Val Lys Val Asn Ile Asn Met Asn Gly Tyr Tyr Ile Val His Tyr
            690                 695                 700

Ala Asp Asp Asp Trp Glu Ala Leu Ile His Gln Leu Lys Ile Asn Pro
705                 710                 715                 720

Tyr Val Leu Ser Asp Lys Asp Arg Ala Asn Leu Ile Asn Asn Ile Phe
            725                 730                 735

Glu Leu Ala Gly Leu Gly Lys Val Pro Leu Lys Arg Ala Phe Asp Leu
            740                 745                 750

Ile Asn Tyr Leu Gly Asn Glu Asn His Thr Ala Pro Ile Thr Glu Ala
            755                 760                 765

Leu Phe Gln Thr Asp Leu Ile Tyr Asn Leu Leu Glu Lys Leu Gly Tyr
            770                 775                 780

Met Asp Leu Ala Ser Arg Leu Val Thr Arg Val Phe Lys Leu Leu Gln
785                 790                 795                 800

Asn Gln Ile Gln Gln Gln Thr Trp Thr Asp Glu Gly Thr Pro Ser Met
            805                 810                 815

Arg Glu Leu Arg Ser Ala Leu Leu Glu Phe Ala Cys Thr His Asn Leu
            820                 825                 830

Gly Asn Cys Ser Thr Thr Ala Met Lys Leu Phe Asp Asp Trp Met Ala
            835                 840                 845

Ser Asn Gly Thr Gln Ser Leu Pro Thr Asp Val Met Thr Thr Val Phe
            850                 855                 860

Lys Val Gly Ala Lys Thr Asp Lys Gly Trp Ser Phe Leu Leu Gly Lys
865                 870                 875                 880

Tyr Ile Ser Ile Gly Ser Glu Ala Glu Lys Asn Lys Ile Leu Glu Ala
            885                 890                 895

Leu Ala Ser Ser Glu Asp Val Arg Lys Leu Tyr Trp Leu Met Lys Ser
            900                 905                 910

Ser Leu Asn Gly Asp Asn Phe Arg Thr Gln Lys Leu Ser Phe Ile Ile
            915                 920                 925

Arg Thr Val Gly Arg His Phe Pro Gly His Leu Leu Ala Trp Asp Phe
            930                 935                 940

Val Lys Glu Asn Trp Asn Lys Leu Val Gln Lys Phe Pro Leu Gly Ser
945                 950                 955                 960

Tyr Thr Ile Gln Asn Ile Val Ala Gly Ser Thr Tyr Leu Phe Ser Thr
            965                 970                 975

Lys Thr His Leu Ser Glu Val Gln Ala Phe Phe Glu Asn Gln Ser Glu
            980                 985                 990
```

```
Ala Thr Phe Arg Leu Arg Cys Val Gln Glu Ala Leu Glu Val Ile Gln
        995                1000                1005

Leu Asn Ile Gln Trp Met Glu Lys Asn Leu Lys Ser Leu Thr Trp
    1010                1015                1020

Trp Leu
    1025

<210> SEQ ID NO 5
<211> LENGTH: 1025
<212> TYPE: PRT
<213> ORGANISM: Homo sapiens
<220> FEATURE:
<221> NAME/KEY: PEPTIDE
<222> LOCATION: (1)..(1025)

<400> SEQUENCE: 5

Met Glu Pro Phe Thr Asn Asp Arg Leu Gln Leu Pro Arg Asn Met Ile
1               5                   10                  15

Glu Asn Ser Met Phe Glu Glu Pro Asp Val Val Asp Leu Ala Lys
            20                  25                  30

Glu Pro Cys Leu His Pro Leu Glu Pro Asp Glu Val Glu Tyr Glu Pro
        35                  40                  45

Arg Gly Ser Arg Leu Leu Val Arg Gly Leu Gly Glu His Glu Met Glu
    50                  55                  60

Glu Asp Glu Glu Asp Tyr Glu Ser Ser Ala Lys Leu Leu Gly Met Ser
65                  70                  75                  80

Phe Met Asn Arg Ser Ser Gly Leu Arg Asn Ser Ala Thr Gly Tyr Arg
                85                  90                  95

Gln Ser Pro Asp Gly Ala Cys Ser Val Pro Ser Ala Arg Thr Met Val
            100                 105                 110

Val Cys Ala Phe Val Ile Val Ala Val Ser Val Ile Met Val Ile
        115                 120                 125

Tyr Leu Leu Pro Arg Cys Thr Phe Thr Lys Glu Gly Cys His Lys Lys
    130                 135                 140

Asn Gln Ser Ile Gly Leu Ile Gln Pro Phe Ala Thr Asn Gly Lys Leu
145                 150                 155                 160

Phe Pro Trp Ala Gln Ile Arg Leu Pro Thr Ala Val Val Pro Leu Arg
                165                 170                 175

Tyr Glu Leu Ser Leu His Pro Asn Leu Thr Ser Met Thr Phe Arg Gly
            180                 185                 190

Ser Val Thr Ile Ser Val Gln Ala Leu Gln Val Thr Trp Asn Ile Ile
        195                 200                 205

Leu His Ser Thr Gly His Asn Ile Ser Arg Val Thr Phe Met Ser Ala
    210                 215                 220

Val Ser Ser Gln Glu Lys Gln Ala Glu Ile Leu Glu Tyr Ala Tyr His
225                 230                 235                 240

Gly Gln Ile Ala Ile Val Ala Pro Glu Ala Leu Leu Ala Gly His Asn
                245                 250                 255

Tyr Thr Leu Lys Ile Glu Tyr Ser Ala Asn Ile Ser Ser Ser Tyr Tyr
            260                 265                 270

Gly Phe Tyr Gly Phe Ser Tyr Thr Asp Glu Ser Asn Glu Lys Lys Tyr
        275                 280                 285

Phe Ala Ala Thr Gln Phe Glu Pro Leu Ala Ala Arg Ser Ala Phe Pro
    290                 295                 300

Cys Phe Asp Glu Pro Ala Phe Lys Ala Thr Phe Ile Ile Lys Ile Ile
```

```
                305                 310                 315                 320
Arg Asp Glu Gln Tyr Thr Ala Leu Ser Asn Met Pro Lys Lys Ser Ser
                    325                 330                 335

Val Val Leu Asp Asp Gly Leu Val Gln Asp Glu Phe Ser Glu Ser Val
                340                 345                 350

Lys Met Ser Thr Tyr Leu Val Ala Phe Ile Val Gly Glu Met Lys Asn
                    355                 360                 365

Leu Ser Gln Asp Val Asn Gly Thr Leu Val Ser Ile Tyr Ala Val Pro
            370                 375                 380

Glu Lys Ile Gly Gln Val His Tyr Ala Leu Glu Thr Val Lys Leu
385                 390                 395                 400

Leu Glu Phe Phe Gln Asn Tyr Phe Glu Ile Gln Tyr Pro Leu Lys Lys
                    405                 410                 415

Leu Asp Leu Val Ala Ile Pro Asp Phe Glu Ala Gly Ala Met Glu Asn
                420                 425                 430

Trp Gly Leu Leu Thr Phe Arg Glu Glu Thr Leu Leu Tyr Asp Ser Asn
            435                 440                 445

Thr Ser Ser Met Ala Asp Arg Lys Leu Val Thr Lys Ile Ile Ala His
        450                 455                 460

Glu Leu Ala His Gln Trp Phe Gly Asn Leu Val Thr Met Lys Trp Trp
465                 470                 475                 480

Asn Asp Leu Trp Leu Asn Glu Gly Phe Ala Thr Phe Met Glu Tyr Phe
                    485                 490                 495

Ser Leu Glu Lys Ile Phe Lys Glu Leu Ser Ser Tyr Glu Asp Phe Leu
                500                 505                 510

Asp Ala Arg Phe Lys Thr Met Lys Lys Asp Ser Leu Asn Ser Ser His
            515                 520                 525

Pro Ile Ser Ser Ser Val Gln Ser Ser Glu Gln Ile Glu Glu Met Phe
        530                 535                 540

Asp Ser Leu Ser Tyr Phe Lys Gly Ser Ser Leu Leu Leu Met Leu Lys
545                 550                 555                 560

Thr Tyr Leu Ser Glu Asp Val Phe Gln His Ala Val Val Leu Tyr Leu
                    565                 570                 575

His Asn His Ser Tyr Ala Ser Ile Gln Ser Asp Asp Leu Trp Asp Ser
                580                 585                 590

Phe Asn Glu Val Thr Asn Gln Thr Leu Asp Val Lys Arg Met Met Lys
            595                 600                 605

Thr Trp Thr Leu Gln Lys Gly Phe Pro Leu Val Thr Val Gln Lys Lys
        610                 615                 620

Gly Lys Glu Leu Phe Ile Gln Gln Glu Arg Phe Phe Leu Asn Met Lys
625                 630                 635                 640

Pro Glu Ile Gln Pro Ser Asp Thr Ser Tyr Leu Trp His Ile Pro Leu
                    645                 650                 655

Ser Tyr Val Thr Glu Gly Arg Asn Tyr Ser Lys Tyr Gln Ser Val Ser
                660                 665                 670

Leu Leu Asp Lys Lys Ser Gly Val Ile Asn Leu Thr Glu Glu Val Leu
            675                 680                 685

Trp Val Lys Val Asn Ile Asn Met Asn Gly Tyr Tyr Ile Val His Tyr
        690                 695                 700

Ala Asp Asp Asp Trp Glu Ala Leu Ile His Gln Leu Lys Ile Asn Pro
705                 710                 715                 720

Tyr Val Leu Ser Asp Lys Asp Arg Ala Asn Leu Ile Asn Asn Ile Phe
                    725                 730                 735
```

-continued

```
Glu Leu Ala Gly Leu Gly Lys Val Pro Leu Lys Arg Ala Phe Asp Leu
            740                 745                 750

Ile Asn Tyr Leu Gly Asn Glu Asn His Thr Thr Pro Ile Thr Glu Ala
            755                 760                 765

Leu Phe Gln Thr Asp Leu Ile Tyr Asn Leu Leu Glu Lys Leu Gly Tyr
            770                 775                 780

Met Asp Leu Ala Ser Arg Leu Val Thr Arg Val Phe Lys Leu Leu Gln
785                 790                 795                 800

Asn Gln Ile Gln Gln Gln Thr Trp Thr Asp Glu Gly Thr Pro Ser Met
            805                 810                 815

Arg Glu Leu Arg Ser Ala Leu Leu Glu Phe Ala Cys Thr His Asn Leu
            820                 825                 830

Gly Asn Cys Ser Thr Thr Ala Met Lys Leu Phe Asp Asp Trp Met Ala
            835                 840                 845

Ser Asn Gly Thr Gln Ser Leu Pro Thr Asp Val Met Thr Thr Val Phe
            850                 855                 860

Lys Val Gly Ala Lys Thr Asp Lys Gly Trp Ser Phe Leu Leu Gly Lys
865                 870                 875                 880

Tyr Ile Ser Ile Gly Ser Glu Ala Glu Lys Asn Lys Ile Leu Glu Ala
            885                 890                 895

Leu Ala Ser Ser Glu Asp Val Arg Lys Leu Tyr Trp Leu Met Lys Ser
            900                 905                 910

Ser Leu Asn Gly Asp Asn Phe Arg Thr Gln Lys Leu Ser Phe Ile Ile
            915                 920                 925

Arg Thr Val Gly Arg His Phe Pro Gly His Leu Leu Ala Trp Asp Phe
            930                 935                 940

Val Lys Glu Asn Trp Asn Lys Leu Val Gln Lys Phe Pro Leu Gly Ser
945                 950                 955                 960

Tyr Thr Ile Gln Asn Ile Val Ala Gly Ser Thr Tyr Leu Phe Ser Thr
            965                 970                 975

Lys Thr His Leu Ser Glu Val Gln Ala Phe Phe Glu Asn Gln Ser Glu
            980                 985                 990

Ala Thr Phe Arg Leu Arg Cys Val Gln Glu Ala Leu Glu Val Ile Gln
            995                 1000                1005

Leu Asn Ile Gln Trp Met Glu Lys Asn Leu Lys Ser Leu Thr Trp
        1010                1015                1020

Trp Leu
    1025

<210> SEQ ID NO 6
<211> LENGTH: 1025
<212> TYPE: PRT
<213> ORGANISM: Homo sapiens
<220> FEATURE:
<221> NAME/KEY: PEPTIDE
<222> LOCATION: (1)..(1025)

<400> SEQUENCE: 6

Met Glu Pro Phe Thr Asn Asp Arg Leu Gln Leu Pro Arg Asn Met Ile
1               5                   10                  15

Glu Asn Ser Met Phe Glu Glu Pro Asp Val Val Asp Leu Ala Lys
            20                  25                  30

Glu Pro Cys Leu His Pro Leu Glu Pro Asp Glu Val Glu Tyr Glu Pro
            35                  40                  45

Arg Gly Ser Arg Leu Leu Val Arg Gly Leu Gly Glu His Glu Met Glu
```

```
                50                  55                  60
Glu Asp Glu Asp Tyr Ser Ser Ala Lys Leu Leu Gly Met Ser
 65                  70                  75                  80

Phe Met Asn Arg Ser Ser Gly Leu Arg Asn Ser Ala Thr Gly Tyr Arg
                 85                  90                  95

Gln Ser Pro Asp Gly Ala Cys Ser Val Pro Ser Ala Arg Thr Met Val
            100                 105                 110

Val Cys Ala Phe Val Ile Val Ala Val Ser Val Ile Met Val Ile
            115                 120                 125

Tyr Leu Leu Pro Arg Cys Thr Phe Thr Lys Glu Gly Cys His Lys Lys
130                 135                 140

Asn Gln Ser Ile Gly Leu Ile Gln Pro Phe Ala Thr Asn Gly Lys Leu
145                 150                 155                 160

Phe Pro Trp Ala Gln Ile Arg Leu Pro Thr Ala Val Val Pro Leu Arg
                165                 170                 175

Tyr Glu Leu Ser Leu His Pro Asn Leu Thr Ser Met Thr Phe Arg Gly
            180                 185                 190

Ser Val Thr Ile Ser Val Gln Ala Leu Gln Val Thr Trp Asn Ile Ile
            195                 200                 205

Leu His Ser Thr Gly His Asn Ile Ser Arg Val Thr Phe Met Ser Ala
210                 215                 220

Val Ser Ser Gln Glu Lys Gln Ala Glu Ile Leu Glu Tyr Ala Tyr His
225                 230                 235                 240

Gly Gln Ile Ala Ile Val Ala Pro Glu Ala Leu Leu Ala Gly His Asn
                245                 250                 255

Tyr Thr Leu Lys Ile Glu Tyr Ser Ala Asn Ile Ser Ser Ser Tyr Tyr
            260                 265                 270

Gly Phe Tyr Gly Phe Ser Tyr Thr Asp Glu Ser Asn Glu Lys Lys Tyr
            275                 280                 285

Phe Ala Ala Thr Gln Phe Glu Pro Leu Ala Ala Arg Ser Ala Phe Pro
290                 295                 300

Cys Phe Asp Glu Pro Ala Phe Lys Ala Thr Phe Ile Ile Lys Ile Ile
305                 310                 315                 320

Arg Asp Glu Gln Tyr Thr Ala Leu Ser Asn Met Pro Lys Lys Ser Ser
                325                 330                 335

Val Val Leu Asp Asp Gly Leu Val Gln Asp Glu Phe Ser Glu Ser Val
            340                 345                 350

Lys Met Ser Thr Tyr Leu Val Ala Phe Ile Val Gly Glu Met Lys Asn
            355                 360                 365

Leu Ser Gln Asp Val Asn Gly Thr Leu Val Ser Ile Tyr Ala Val Pro
370                 375                 380

Glu Lys Ile Gly Gln Val His Tyr Ala Leu Glu Thr Val Lys Leu
385                 390                 395                 400

Leu Glu Phe Phe Gln Asn Tyr Phe Glu Ile Gln Tyr Pro Leu Lys Lys
                405                 410                 415

Leu Asp Leu Val Ala Ile Pro Asp Phe Glu Ala Gly Ala Met Glu Asn
            420                 425                 430

Trp Gly Leu Leu Thr Phe Arg Glu Glu Thr Leu Leu Tyr Asp Ser Asn
            435                 440                 445

Thr Ser Ser Met Ala Asp Arg Lys Leu Val Thr Lys Ile Ile Ala His
450                 455                 460

Glu Leu Ala His Gln Trp Phe Gly Asn Leu Val Thr Met Lys Trp Trp
465                 470                 475                 480
```

-continued

```
Asn Asp Leu Trp Leu Asn Glu Gly Phe Ala Thr Phe Met Glu Tyr Phe
            485                 490                 495
Ser Leu Glu Lys Ile Phe Lys Glu Leu Ser Ser Tyr Glu Asp Phe Leu
            500                 505                 510
Asp Ala Arg Phe Lys Thr Met Lys Lys Asp Ser Leu Asn Ser Ser His
            515                 520                 525
Pro Ile Ser Ser Ser Val Gln Ser Ser Glu Gln Ile Glu Glu Met Phe
            530                 535                 540
Asp Ser Leu Ser Tyr Phe Lys Gly Ser Ser Leu Leu Met Leu Lys
545                 550                 555                 560
Thr Tyr Leu Ser Glu Asp Val Phe Gln His Ala Val Val Leu Tyr Leu
            565                 570                 575
His Asn His Ser Tyr Ala Ser Ile Gln Ser Asp Asp Leu Trp Asp Ser
            580                 585                 590
Phe Asn Glu Val Thr Asn Gln Thr Leu Asp Val Lys Arg Met Met Lys
            595                 600                 605
Thr Trp Thr Leu Gln Lys Gly Phe Pro Leu Val Thr Val Gln Lys Lys
            610                 615                 620
Gly Lys Glu Leu Phe Ile Gln Gln Glu Arg Phe Phe Leu Asn Met Lys
625                 630                 635                 640
Pro Glu Ile Gln Pro Ser Asp Thr Ser Tyr Leu Trp His Ile Pro Leu
            645                 650                 655
Ser Tyr Val Thr Glu Gly Arg Asn Tyr Ser Lys Tyr Gln Ser Val Ser
            660                 665                 670
Leu Leu Asp Lys Lys Ser Gly Val Ile Asn Leu Thr Glu Glu Val Leu
            675                 680                 685
Trp Val Lys Val Asn Ile Asn Met Asn Gly Tyr Tyr Ile Val His Tyr
            690                 695                 700
Ala Asp Asp Asp Trp Glu Ala Leu Ile His Gln Leu Lys Ile Asn Pro
705                 710                 715                 720
Tyr Val Leu Ser Asp Lys Asp Arg Ala Asn Leu Ile Asn Asn Ile Phe
            725                 730                 735
Glu Leu Ala Gly Leu Gly Lys Val Pro Leu Lys Arg Ala Phe Asp Leu
            740                 745                 750
Ile Asn Tyr Leu Gly Asn Glu Asn His Thr Ala Pro Ile Thr Glu Ala
            755                 760                 765
Leu Phe Gln Thr Asp Leu Ile Tyr Asn Leu Leu Glu Lys Leu Gly Tyr
            770                 775                 780
Met Asp Leu Ala Ser Arg Leu Val Thr Arg Val Phe Lys Leu Leu Gln
785                 790                 795                 800
Asn Gln Ile Gln Gln Gln Thr Trp Thr Asp Glu Gly Thr Pro Ser Met
            805                 810                 815
Arg Glu Leu Arg Ser Ala Leu Leu Glu Phe Ala Cys Thr His Asn Leu
            820                 825                 830
Gly Asn Cys Ser Thr Thr Ala Met Lys Leu Phe Asp Asp Trp Met Ala
            835                 840                 845
Ser Asn Gly Thr Gln Ser Leu Pro Thr Asp Val Met Thr Thr Val Phe
            850                 855                 860
Lys Val Gly Ala Lys Thr Asp Lys Gly Trp Ser Phe Leu Leu Gly Lys
865                 870                 875                 880
Tyr Ile Ser Ile Gly Ser Glu Ala Glu Lys Asn Lys Ile Leu Glu Ala
            885                 890                 895
```

```
Leu Ala Ser Ser Glu Asp Val Arg Lys Leu Tyr Trp Leu Met Lys Ser
            900                 905                 910

Ser Leu Asn Gly Asp Asn Phe Arg Thr Gln Lys Leu Ser Phe Ile Ile
    915                 920                 925

Arg Thr Val Gly Arg His Phe Pro Gly His Leu Leu Ala Trp Asp Phe
930                 935                 940

Val Lys Glu Asn Trp Asn Lys Leu Val Gln Lys Phe Pro Leu Gly Ser
945                 950                 955                 960

Tyr Thr Val Gln Asn Ile Val Ala Gly Ser Thr Tyr Leu Phe Ser Thr
                965                 970                 975

Lys Thr His Leu Ser Glu Val Gln Ala Phe Phe Glu Asn Gln Ser Glu
            980                 985                 990

Ala Thr Phe Arg Leu Arg Cys Val Gln Glu Ala Leu Glu Val Ile Gln
        995                 1000                1005

Leu Asn Ile Gln Trp Met Glu Lys Asn Leu Lys Ser Leu Thr Trp
    1010                1015                1020

Trp Leu
    1025

<210> SEQ ID NO 7
<211> LENGTH: 894
<212> TYPE: PRT
<213> ORGANISM: Homo sapiens
<220> FEATURE:
<221> NAME/KEY: PEPTIDE
<222> LOCATION: (1)..(894)

<400> SEQUENCE: 7

Pro Arg Cys Thr Phe Thr Lys Glu Gly Cys His Lys Lys Asn Gln Ser
1               5                   10                  15

Ile Gly Leu Ile Gln Pro Phe Ala Thr Asn Gly Lys Leu Phe Pro Trp
            20                  25                  30

Ala Gln Ile Arg Leu Pro Thr Ala Val Val Pro Leu Arg Tyr Glu Leu
        35                  40                  45

Ser Leu His Pro Asn Leu Thr Ser Met Thr Phe Arg Gly Ser Val Thr
    50                  55                  60

Ile Ser Val Gln Ala Leu Gln Val Thr Trp Asn Ile Ile Leu His Ser
65                  70                  75                  80

Thr Gly His Asn Ile Ser Arg Val Thr Phe Met Ser Ala Val Ser Ser
                85                  90                  95

Gln Glu Lys Gln Ala Glu Ile Leu Glu Tyr Ala Tyr His Gly Gln Ile
            100                 105                 110

Ala Ile Val Ala Pro Glu Ala Leu Leu Ala Gly His Asn Tyr Thr Leu
        115                 120                 125

Lys Ile Glu Tyr Ser Ala Asn Ile Ser Ser Ser Tyr Tyr Gly Phe Tyr
    130                 135                 140

Gly Phe Ser Tyr Thr Asp Glu Ser Asn Glu Lys Lys Tyr Phe Ala Ala
145                 150                 155                 160

Thr Gln Phe Glu Pro Leu Ala Ala Arg Ser Ala Phe Pro Cys Phe Asp
                165                 170                 175

Glu Pro Ala Phe Lys Ala Thr Phe Ile Ile Lys Ile Ile Arg Asp Glu
            180                 185                 190

Gln Tyr Thr Ala Leu Ser Asn Met Pro Lys Lys Ser Ser Val Val Leu
        195                 200                 205

Asp Asp Gly Leu Val Gln Asp Glu Phe Ser Glu Ser Val Lys Met Ser
    210                 215                 220
```

-continued

Thr Tyr Leu Val Ala Phe Ile Val Gly Glu Met Lys Asn Leu Ser Gln
225                 230                 235                 240

Asp Val Asn Gly Thr Leu Val Ser Ile Tyr Ala Val Pro Glu Lys Ile
            245                 250                 255

Gly Gln Val His Tyr Ala Leu Glu Thr Thr Val Lys Leu Leu Glu Phe
        260                 265                 270

Phe Gln Asn Tyr Phe Glu Ile Gln Tyr Pro Leu Lys Lys Leu Asp Leu
    275                 280                 285

Val Ala Ile Pro Asp Phe Glu Ala Gly Ala Met Glu Asn Trp Gly Leu
290                 295                 300

Leu Thr Phe Arg Glu Glu Thr Leu Leu Tyr Asp Ser Asn Thr Ser Ser
305                 310                 315                 320

Met Ala Asp Arg Lys Leu Val Thr Lys Ile Ile Ala His Glu Leu Ala
            325                 330                 335

His Gln Trp Phe Gly Asn Leu Val Thr Met Lys Trp Trp Asn Asp Leu
        340                 345                 350

Trp Leu Asn Glu Gly Phe Ala Thr Phe Met Glu Tyr Phe Ser Leu Glu
    355                 360                 365

Lys Ile Phe Lys Glu Leu Ser Ser Tyr Glu Asp Phe Leu Asp Ala Arg
370                 375                 380

Phe Lys Thr Met Lys Lys Asp Ser Leu Asn Ser Ser His Pro Ile Ser
385                 390                 395                 400

Ser Ser Val Gln Ser Ser Glu Gln Ile Glu Glu Met Phe Asp Ser Leu
            405                 410                 415

Ser Tyr Phe Lys Gly Ser Ser Leu Leu Leu Met Leu Lys Thr Tyr Leu
        420                 425                 430

Ser Glu Asp Val Phe Gln His Ala Val Val Leu Tyr Leu His Asn His
    435                 440                 445

Ser Tyr Ala Ser Ile Gln Ser Asp Asp Leu Trp Asp Ser Phe Asn Glu
450                 455                 460

Val Thr Asn Gln Thr Leu Asp Val Lys Arg Met Met Lys Thr Trp Thr
465                 470                 475                 480

Leu Gln Lys Gly Phe Pro Leu Val Thr Val Gln Lys Lys Gly Lys Glu
            485                 490                 495

Leu Phe Ile Gln Gln Glu Arg Phe Phe Leu Asn Met Lys Pro Glu Ile
        500                 505                 510

Gln Pro Ser Asp Thr Ser Tyr Leu Trp His Ile Pro Leu Ser Tyr Val
    515                 520                 525

Thr Glu Gly Arg Asn Tyr Ser Lys Tyr Gln Ser Val Ser Leu Leu Asp
530                 535                 540

Lys Lys Ser Gly Val Ile Asn Leu Thr Glu Glu Val Leu Trp Val Lys
545                 550                 555                 560

Val Asn Ile Asn Met Asn Gly Tyr Tyr Ile Val His Tyr Ala Asp Asp
            565                 570                 575

Asp Trp Glu Ala Leu Ile His Gln Leu Lys Ile Asn Pro Tyr Val Leu
        580                 585                 590

Ser Asp Lys Asp Arg Ala Asn Leu Ile Asn Asn Ile Phe Glu Leu Ala
    595                 600                 605

Gly Leu Gly Lys Val Pro Leu Lys Arg Ala Phe Asp Leu Ile Asn Tyr
610                 615                 620

Leu Gly Asn Glu Asn His Thr Ala Pro Ile Thr Glu Ala Leu Phe Gln
625                 630                 635                 640

```
Thr Asp Leu Ile Tyr Asn Leu Leu Glu Lys Leu Gly Tyr Met Asp Leu
                645                 650                 655

Ala Ser Arg Leu Val Thr Arg Val Phe Lys Leu Leu Gln Asn Gln Ile
            660                 665                 670

Gln Gln Gln Thr Trp Thr Asp Glu Gly Thr Pro Ser Met Arg Glu Leu
        675                 680                 685

Arg Ser Ala Leu Leu Glu Phe Ala Cys Thr His Asn Leu Gly Asn Cys
    690                 695                 700

Ser Thr Thr Ala Met Lys Leu Phe Asp Asp Trp Met Ala Ser Asn Gly
705                 710                 715                 720

Thr Gln Ser Leu Pro Thr Asp Val Met Thr Thr Val Phe Lys Val Gly
                725                 730                 735

Ala Lys Thr Asp Lys Gly Trp Ser Phe Leu Leu Gly Lys Tyr Ile Ser
            740                 745                 750

Ile Gly Ser Glu Ala Glu Lys Asn Lys Ile Leu Glu Ala Leu Ala Ser
        755                 760                 765

Ser Glu Asp Val Arg Lys Leu Tyr Trp Leu Met Lys Ser Ser Leu Asn
    770                 775                 780

Gly Asp Asn Phe Arg Thr Gln Lys Leu Ser Phe Ile Ile Arg Thr Val
785                 790                 795                 800

Gly Arg His Phe Pro Gly His Leu Leu Ala Trp Asp Phe Val Lys Glu
                805                 810                 815

Asn Trp Asn Lys Leu Val Gln Lys Phe Pro Leu Gly Ser Tyr Thr Ile
            820                 825                 830

Gln Asn Ile Val Ala Gly Ser Thr Tyr Leu Phe Ser Thr Lys Thr His
        835                 840                 845

Leu Ser Glu Val Gln Ala Phe Phe Glu Asn Gln Ser Glu Ala Thr Phe
    850                 855                 860

Arg Leu Arg Cys Val Gln Glu Ala Leu Glu Val Ile Gln Leu Asn Ile
865                 870                 875                 880

Gln Trp Met Glu Lys Asn Leu Lys Ser Leu Thr Trp Trp Leu
                885                 890

<210> SEQ ID NO 8
<211> LENGTH: 951
<212> TYPE: PRT
<213> ORGANISM: Homo sapiens
<220> FEATURE:
<221> NAME/KEY: PEPTIDE
<222> LOCATION: (1)..(951)

<400> SEQUENCE: 8

Lys Leu Leu Gly Met Ser Phe Met Asn Arg Ser Ser Gly Leu Arg Asn
1               5                   10                  15

Ser Ala Thr Gly Tyr Arg Gln Ser Pro Asp Gly Ala Cys Ser Val Pro
            20                  25                  30

Ser Ala Arg Thr Met Val Val Cys Ala Phe Val Ile Val Ala Val
        35                  40                  45

Ser Val Ile Met Val Ile Tyr Leu Leu Pro Arg Cys Thr Phe Thr Lys
    50                  55                  60

Glu Gly Cys His Lys Lys Asn Gln Ser Ile Gly Leu Ile Gln Pro Phe
65                  70                  75                  80

Ala Thr Asn Gly Lys Leu Phe Pro Trp Ala Gln Ile Arg Leu Pro Thr
                85                  90                  95

Ala Val Val Pro Leu Arg Tyr Glu Leu Ser Leu His Pro Asn Leu Thr
            100                 105                 110
```

```
Ser Met Thr Phe Arg Gly Ser Val Thr Ile Ser Val Gln Ala Leu Gln
        115                 120                 125

Val Thr Trp Asn Ile Ile Leu His Ser Thr Gly His Asn Ile Ser Arg
130                 135                 140

Val Thr Phe Met Ser Ala Val Ser Ser Gln Glu Lys Gln Ala Glu Ile
145                 150                 155                 160

Leu Glu Tyr Ala Tyr His Gly Gln Ile Ala Ile Val Ala Pro Glu Ala
                165                 170                 175

Leu Leu Ala Gly His Asn Tyr Thr Leu Lys Ile Glu Tyr Ser Ala Asn
                180                 185                 190

Ile Ser Ser Ser Tyr Tyr Gly Phe Tyr Gly Phe Ser Tyr Thr Asp Glu
                195                 200                 205

Ser Asn Glu Lys Lys Tyr Phe Ala Ala Thr Gln Phe Glu Pro Leu Ala
        210                 215                 220

Ala Arg Ser Ala Phe Pro Cys Phe Asp Glu Pro Ala Phe Lys Ala Thr
225                 230                 235                 240

Phe Ile Ile Lys Ile Ile Arg Asp Glu Gln Tyr Thr Ala Leu Ser Asn
                245                 250                 255

Met Pro Lys Lys Ser Ser Val Val Leu Asp Asp Gly Leu Val Gln Asp
        260                 265                 270

Glu Phe Ser Glu Ser Val Lys Met Ser Thr Tyr Leu Val Ala Phe Ile
        275                 280                 285

Val Gly Glu Met Lys Asn Leu Ser Gln Asp Val Asn Gly Thr Leu Val
        290                 295                 300

Ser Ile Tyr Ala Val Pro Glu Lys Ile Gly Gln Val His Tyr Ala Leu
305                 310                 315                 320

Glu Thr Thr Val Lys Leu Leu Glu Phe Phe Gln Asn Tyr Phe Glu Ile
                325                 330                 335

Gln Tyr Pro Leu Lys Lys Leu Asp Leu Val Ala Ile Pro Asp Phe Glu
                340                 345                 350

Ala Gly Ala Met Glu Asn Trp Gly Leu Leu Thr Phe Arg Glu Glu Thr
                355                 360                 365

Leu Leu Tyr Asp Ser Asn Thr Ser Ser Met Ala Asp Arg Lys Leu Val
        370                 375                 380

Thr Lys Ile Ile Ala His Glu Leu Ala His Gln Trp Phe Gly Asn Leu
385                 390                 395                 400

Val Thr Met Lys Trp Trp Asn Asp Leu Trp Leu Asn Glu Gly Phe Ala
                405                 410                 415

Thr Phe Met Glu Tyr Phe Ser Leu Glu Lys Ile Phe Lys Glu Leu Ser
                420                 425                 430

Ser Tyr Glu Asp Phe Leu Asp Ala Arg Phe Lys Thr Met Lys Lys Asp
        435                 440                 445

Ser Leu Asn Ser Ser His Pro Ile Ser Ser Val Gln Ser Ser Glu
        450                 455                 460

Gln Ile Glu Glu Met Phe Asp Ser Leu Ser Tyr Phe Lys Gly Ser Ser
465                 470                 475                 480

Leu Leu Leu Met Leu Lys Thr Tyr Leu Ser Glu Asp Val Phe Gln His
                485                 490                 495

Ala Val Val Leu Tyr Leu His Asn His Ser Tyr Ala Ser Ile Gln Ser
                500                 505                 510

Asp Asp Leu Trp Asp Ser Phe Asn Glu Val Thr Asn Gln Thr Leu Asp
        515                 520                 525
```

```
Val Lys Arg Met Met Lys Thr Trp Thr Leu Gln Lys Gly Phe Pro Leu
530                 535                 540
Val Thr Val Gln Lys Lys Gly Lys Glu Leu Phe Ile Gln Gln Glu Arg
545                 550                 555                 560
Phe Phe Leu Asn Met Lys Pro Glu Ile Gln Pro Ser Asp Thr Ser Tyr
                565                 570                 575
Leu Trp His Ile Pro Leu Ser Tyr Val Thr Glu Gly Arg Asn Tyr Ser
                580                 585                 590
Lys Tyr Gln Ser Val Ser Leu Asp Lys Lys Ser Gly Val Ile Asn
            595                 600                 605
Leu Thr Glu Glu Val Leu Trp Val Lys Val Asn Ile Asn Met Asn Gly
610                 615                 620
Tyr Tyr Ile Val His Tyr Ala Asp Asp Asp Trp Glu Ala Leu Ile His
625                 630                 635                 640
Gln Leu Lys Ile Asn Pro Tyr Val Leu Ser Asp Lys Asp Arg Ala Asn
                645                 650                 655
Leu Ile Asn Asn Ile Phe Glu Leu Ala Gly Leu Gly Lys Val Pro Leu
                660                 665                 670
Lys Arg Ala Phe Asp Leu Ile Asn Tyr Leu Gly Asn Glu Asn His Thr
            675                 680                 685
Ala Pro Ile Thr Glu Ala Leu Phe Gln Thr Asp Leu Ile Tyr Asn Leu
690                 695                 700
Leu Glu Lys Leu Gly Tyr Met Asp Leu Ala Ser Arg Leu Val Thr Arg
705                 710                 715                 720
Val Phe Lys Leu Leu Gln Asn Gln Ile Gln Gln Gln Thr Trp Thr Asp
                725                 730                 735
Glu Gly Thr Pro Ser Met Arg Glu Leu Arg Ser Ala Leu Leu Glu Phe
                740                 745                 750
Ala Cys Thr His Asn Leu Gly Asn Cys Ser Thr Thr Ala Met Lys Leu
            755                 760                 765
Phe Asp Asp Trp Met Ala Ser Asn Gly Thr Gln Ser Leu Pro Thr Asp
770                 775                 780
Val Met Thr Thr Val Phe Lys Val Gly Ala Lys Thr Asp Lys Gly Trp
785                 790                 795                 800
Ser Phe Leu Leu Gly Lys Tyr Ile Ser Ile Gly Ser Glu Ala Glu Lys
                805                 810                 815
Asn Lys Ile Leu Glu Ala Leu Ala Ser Ser Glu Asp Val Arg Lys Leu
                820                 825                 830
Tyr Trp Leu Met Lys Ser Ser Leu Asn Gly Asp Asn Phe Arg Thr Gln
            835                 840                 845
Lys Leu Ser Phe Ile Ile Arg Thr Val Gly Arg His Phe Pro Gly His
850                 855                 860
Leu Leu Ala Trp Asp Phe Val Lys Glu Asn Trp Asn Lys Leu Val Gln
865                 870                 875                 880
Lys Phe Pro Leu Gly Ser Tyr Thr Ile Gln Asn Ile Val Ala Gly Ser
                885                 890                 895
Thr Tyr Leu Phe Ser Thr Lys Thr His Leu Ser Glu Val Gln Ala Phe
                900                 905                 910
Phe Glu Asn Gln Ser Glu Ala Thr Phe Arg Leu Arg Cys Val Gln Glu
            915                 920                 925
Ala Leu Glu Val Ile Gln Leu Asn Ile Gln Trp Met Glu Lys Asn Leu
930                 935                 940
Lys Ser Leu Thr Trp Trp Leu
```

```
945             950

<210> SEQ ID NO 9
<211> LENGTH: 894
<212> TYPE: PRT
<213> ORGANISM: Homo sapiens
<220> FEATURE:
<221> NAME/KEY: PEPTIDE
<222> LOCATION: (1)..(894)

<400> SEQUENCE: 9

Pro Arg Cys Thr Phe Thr Lys Glu Gly Cys His Lys Asn Gln Ser
1               5                   10                  15

Ile Gly Leu Ile Gln Pro Phe Ala Thr Asn Gly Lys Leu Phe Pro Trp
            20                  25                  30

Ala Gln Ile Arg Leu Pro Thr Ala Val Val Pro Leu Arg Tyr Glu Leu
        35                  40                  45

Ser Leu His Pro Asn Leu Thr Ser Met Thr Phe Arg Gly Ser Val Thr
    50                  55                  60

Ile Ser Val Gln Ala Leu Gln Val Thr Trp Asn Ile Ile Leu His Ser
65                  70                  75                  80

Thr Gly His Asn Ile Ser Arg Val Thr Phe Met Ser Ala Val Ser Ser
                85                  90                  95

Gln Glu Lys Gln Ala Glu Ile Leu Glu Tyr Ala Tyr His Gly Gln Ile
            100                 105                 110

Ala Ile Val Ala Pro Glu Ala Leu Leu Ala Gly His Asn Tyr Thr Leu
        115                 120                 125

Lys Ile Glu Tyr Ser Ala Asn Ile Ser Ser Ser Tyr Tyr Gly Phe Tyr
    130                 135                 140

Gly Phe Ser Tyr Thr Asp Glu Ser Asn Glu Lys Lys Tyr Phe Ala Ala
145                 150                 155                 160

Thr Gln Phe Glu Pro Leu Ala Ala Arg Ser Ala Phe Pro Cys Phe Asp
                165                 170                 175

Glu Pro Ala Phe Lys Ala Thr Phe Ile Ile Lys Ile Ile Arg Asp Glu
            180                 185                 190

Gln Tyr Thr Ala Leu Ser Asn Met Pro Lys Lys Ser Ser Val Val Leu
        195                 200                 205

Asp Asp Gly Leu Val Gln Asp Glu Phe Ser Glu Ser Val Lys Met Ser
    210                 215                 220

Thr Tyr Leu Val Ala Phe Ile Val Gly Glu Met Lys Asn Leu Ser Gln
225                 230                 235                 240

Asp Val Asn Gly Thr Leu Val Ser Ile Tyr Ala Val Pro Glu Lys Ile
                245                 250                 255

Gly Gln Val His Tyr Ala Leu Glu Thr Thr Val Lys Leu Leu Glu Phe
            260                 265                 270

Phe Gln Asn Tyr Phe Glu Ile Gln Tyr Pro Leu Lys Lys Leu Asp Leu
        275                 280                 285

Val Ala Ile Pro Asp Phe Glu Ala Gly Ala Met Glu Asn Trp Gly Leu
    290                 295                 300

Leu Thr Phe Arg Glu Glu Thr Leu Leu Tyr Asp Ser Asn Thr Ser Ser
305                 310                 315                 320

Met Ala Asp Arg Lys Leu Val Thr Lys Ile Ile Ala His Glu Leu Ala
                325                 330                 335

His Gln Trp Phe Gly Asn Leu Val Thr Met Lys Trp Asn Asp Leu
            340                 345                 350
```

```
Trp Leu Asn Glu Gly Phe Ala Thr Phe Met Glu Tyr Phe Ser Leu Glu
            355                 360                 365
Lys Ile Phe Lys Glu Leu Ser Ser Tyr Glu Asp Phe Leu Asp Ala Arg
        370                 375                 380
Phe Lys Thr Met Lys Lys Asp Ser Leu Asn Ser Ser His Pro Ile Ser
385                 390                 395                 400
Ser Ser Val Gln Ser Ser Glu Gln Ile Glu Met Phe Asp Ser Leu
                405                 410                 415
Ser Tyr Phe Lys Gly Ser Ser Leu Leu Leu Met Leu Lys Thr Tyr Leu
                420                 425                 430
Ser Glu Asp Val Phe Gln His Ala Val Val Leu Tyr Leu His Asn His
            435                 440                 445
Ser Tyr Ala Ser Ile Gln Ser Asp Asp Leu Trp Asp Ser Phe Asn Glu
        450                 455                 460
Val Thr Asn Gln Thr Leu Asp Val Lys Arg Met Met Lys Thr Trp Thr
465                 470                 475                 480
Leu Gln Lys Gly Phe Pro Leu Val Thr Val Gln Lys Lys Gly Lys Glu
                485                 490                 495
Leu Phe Ile Gln Gln Glu Arg Phe Phe Leu Asn Met Lys Pro Glu Ile
                500                 505                 510
Gln Pro Ser Asp Thr Ser Tyr Leu Trp His Ile Pro Leu Ser Tyr Val
            515                 520                 525
Thr Glu Gly Arg Asn Tyr Ser Lys Tyr Gln Ser Val Ser Leu Leu Asp
        530                 535                 540
Lys Lys Ser Gly Val Ile Asn Leu Thr Glu Glu Val Leu Trp Val Lys
545                 550                 555                 560
Val Asn Ile Asn Met Asn Gly Tyr Tyr Ile Val His Tyr Ala Asp Asp
                565                 570                 575
Asp Trp Glu Ala Leu Ile His Gln Leu Lys Ile Asn Pro Tyr Val Leu
            580                 585                 590
Ser Asp Lys Asp Arg Ala Asn Leu Ile Asn Asn Ile Phe Glu Leu Ala
        595                 600                 605
Gly Leu Gly Lys Val Pro Leu Lys Arg Ala Phe Asp Leu Ile Asn Tyr
610                 615                 620
Leu Gly Asn Glu Asn His Thr Ala Pro Ile Thr Glu Ala Leu Phe Gln
625                 630                 635                 640
Thr Asp Leu Ile Tyr Asn Leu Leu Glu Lys Leu Gly Tyr Met Asp Leu
            645                 650                 655
Ala Ser Arg Leu Val Thr Arg Val Phe Lys Leu Leu Gln Asn Gln Ile
        660                 665                 670
Gln Gln Gln Thr Trp Thr Asp Glu Gly Thr Pro Ser Met Arg Glu Leu
                675                 680                 685
Arg Ser Ala Leu Leu Glu Phe Ala Cys Thr His Asn Leu Gly Asn Cys
        690                 695                 700
Ser Thr Thr Ala Met Lys Leu Phe Asp Asp Trp Met Ala Ser Asn Gly
705                 710                 715                 720
Thr Gln Ser Leu Pro Thr Asp Val Met Thr Val Phe Lys Val Gly
                725                 730                 735
Ala Lys Thr Asp Lys Gly Trp Ser Phe Leu Leu Gly Lys Tyr Ile Ser
            740                 745                 750
Ile Gly Ser Glu Ala Glu Lys Asn Lys Ile Leu Glu Ala Leu Ala Ser
        755                 760                 765
Ser Glu Asp Val Arg Lys Leu Tyr Trp Leu Met Lys Ser Ser Leu Asn
```

```
                    770                 775                 780
Gly Asp Asn Phe Arg Thr Gln Lys Leu Ser Phe Ile Ile Arg Thr Val
785                 790                 795                 800

Gly Arg His Phe Pro Gly His Leu Leu Ala Trp Asp Phe Val Lys Glu
                805                 810                 815

Asn Trp Asn Lys Leu Val Gln Lys Phe Pro Leu Gly Ser Tyr Thr Ile
            820                 825                 830

Gln Asn Ile Val Ala Gly Ser Thr Tyr Leu Phe Ser Thr Lys Thr His
        835                 840                 845

Leu Ser Glu Val Gln Ala Phe Phe Glu Asn Gln Ser Glu Ala Thr Phe
850                 855                 860

Arg Leu Arg Cys Val Gln Glu Ala Leu Glu Val Ile Gln Leu Asn Ile
865                 870                 875                 880

Gln Trp Met Glu Lys Asn Leu Lys Ser Leu Thr Trp Trp Leu
                885                 890

<210> SEQ ID NO 10
<211> LENGTH: 894
<212> TYPE: PRT
<213> ORGANISM: Homo sapiens
<220> FEATURE:
<221> NAME/KEY: PEPTIDE
<222> LOCATION: (1)..(894)

<400> SEQUENCE: 10

Pro Arg Cys Thr Phe Thr Lys Glu Gly Cys His Lys Lys Asn Gln Ser
1               5                   10                  15

Ile Gly Leu Ile Gln Pro Phe Ala Thr Asn Gly Lys Leu Phe Pro Trp
            20                  25                  30

Ala Gln Ile Arg Leu Pro Thr Ala Val Val Pro Leu Arg Tyr Glu Leu
        35                  40                  45

Ser Leu His Pro Asn Leu Thr Ser Met Thr Phe Arg Gly Ser Val Thr
    50                  55                  60

Ile Ser Val Gln Ala Leu Gln Val Thr Trp Asn Ile Ile Leu His Ser
65                  70                  75                  80

Thr Gly His Asn Ile Ser Arg Val Thr Phe Met Ser Ala Val Ser Ser
                85                  90                  95

Gln Glu Lys Gln Ala Glu Ile Leu Glu Tyr Ala Tyr His Gly Gln Ile
            100                 105                 110

Ala Ile Val Ala Pro Glu Ala Leu Leu Ala Gly His Asn Tyr Thr Leu
        115                 120                 125

Lys Ile Glu Tyr Ser Ala Asn Ile Ser Ser Ser Tyr Tyr Gly Phe Tyr
    130                 135                 140

Gly Phe Ser Tyr Thr Asp Glu Ser Asn Glu Lys Lys Tyr Phe Ala Ala
145                 150                 155                 160

Thr Gln Phe Glu Pro Leu Ala Ala Arg Ser Ala Phe Pro Cys Phe Asp
                165                 170                 175

Glu Pro Ala Phe Lys Ala Thr Phe Ile Ile Lys Ile Ile Arg Asp Glu
            180                 185                 190

Gln Tyr Thr Ala Leu Ser Asn Met Pro Lys Lys Ser Ser Val Val Leu
        195                 200                 205

Asp Asp Gly Leu Val Gln Asp Glu Phe Ser Glu Ser Val Lys Met Ser
    210                 215                 220

Thr Tyr Leu Val Ala Phe Ile Val Gly Glu Met Lys Asn Leu Ser Gln
225                 230                 235                 240
```

```
Asp Val Asn Gly Thr Leu Val Ser Ile Tyr Ala Val Pro Glu Lys Ile
                245                 250                 255

Gly Gln Val His Tyr Ala Leu Glu Thr Thr Val Lys Leu Leu Glu Phe
            260                 265                 270

Phe Gln Asn Tyr Phe Glu Ile Gln Tyr Pro Leu Lys Lys Leu Asp Leu
        275                 280                 285

Val Ala Ile Pro Asp Phe Glu Ala Gly Ala Met Glu Asn Trp Gly Leu
    290                 295                 300

Leu Thr Phe Arg Glu Glu Thr Leu Leu Tyr Asp Ser Asn Thr Ser Ser
305                 310                 315                 320

Met Ala Asp Arg Lys Leu Val Thr Lys Ile Ile Ala His Glu Leu Ala
                325                 330                 335

His Gln Trp Phe Gly Asn Leu Val Thr Met Lys Trp Trp Asn Asp Leu
            340                 345                 350

Trp Leu Asn Glu Gly Phe Ala Thr Phe Met Glu Tyr Phe Ser Leu Glu
        355                 360                 365

Lys Ile Phe Lys Glu Leu Ser Ser Tyr Glu Asp Phe Leu Asp Ala Arg
    370                 375                 380

Phe Lys Thr Met Lys Lys Asp Ser Leu Asn Ser Ser His Pro Ile Ser
385                 390                 395                 400

Ser Ser Val Gln Ser Ser Glu Gln Ile Glu Glu Met Phe Asp Ser Leu
                405                 410                 415

Ser Tyr Phe Lys Gly Ser Ser Leu Leu Leu Met Leu Lys Thr Tyr Leu
            420                 425                 430

Ser Glu Asp Val Phe Gln His Ala Val Val Leu Tyr Leu His Asn His
        435                 440                 445

Ser Tyr Ala Ser Ile Gln Ser Asp Asp Leu Trp Asp Ser Phe Asn Glu
    450                 455                 460

Val Thr Asn Gln Thr Leu Asp Val Lys Arg Met Met Lys Thr Trp Thr
465                 470                 475                 480

Leu Gln Lys Gly Phe Pro Leu Val Thr Val Gln Lys Lys Gly Lys Glu
                485                 490                 495

Leu Phe Ile Gln Gln Glu Arg Phe Phe Leu Asn Met Lys Pro Glu Ile
            500                 505                 510

Gln Pro Ser Asp Thr Ser Tyr Leu Trp His Ile Pro Leu Ser Tyr Val
        515                 520                 525

Thr Glu Gly Arg Asn Tyr Ser Lys Tyr Gln Ser Val Ser Leu Leu Asp
    530                 535                 540

Lys Lys Ser Gly Val Ile Asn Leu Thr Glu Glu Val Leu Trp Val Lys
545                 550                 555                 560

Val Asn Ile Asn Met Asn Gly Tyr Tyr Ile Val His Tyr Ala Asp Asp
                565                 570                 575

Asp Trp Glu Ala Leu Ile His Gln Leu Lys Ile Asn Pro Tyr Val Leu
            580                 585                 590

Ser Asp Lys Asp Arg Ala Asn Leu Ile Asn Asn Ile Phe Glu Leu Ala
        595                 600                 605

Gly Leu Gly Lys Val Pro Leu Lys Arg Ala Phe Asp Leu Ile Asn Tyr
    610                 615                 620

Leu Gly Asn Glu Asn His Thr Thr Pro Ile Thr Glu Ala Leu Phe Gln
625                 630                 635                 640

Thr Asp Leu Ile Tyr Asn Leu Leu Glu Lys Leu Gly Tyr Met Asp Leu
                645                 650                 655

Ala Ser Arg Leu Val Thr Arg Val Phe Lys Leu Leu Gln Asn Gln Ile
```

```
        660                 665                 670
Gln Gln Gln Thr Trp Thr Asp Glu Gly Thr Pro Ser Met Arg Glu Leu
            675                 680                 685

Arg Ser Ala Leu Leu Glu Phe Ala Cys Thr His Asn Leu Gly Asn Cys
690                 695                 700

Ser Thr Thr Ala Met Lys Leu Phe Asp Asp Trp Met Ala Ser Asn Gly
705                 710                 715                 720

Thr Gln Ser Leu Pro Thr Asp Val Met Thr Thr Val Phe Lys Val Gly
                725                 730                 735

Ala Lys Thr Asp Lys Gly Trp Ser Phe Leu Leu Gly Lys Tyr Ile Ser
            740                 745                 750

Ile Gly Ser Glu Ala Glu Lys Asn Lys Ile Leu Glu Ala Leu Ala Ser
        755                 760                 765

Ser Glu Asp Val Arg Lys Leu Tyr Trp Leu Met Lys Ser Ser Leu Asn
    770                 775                 780

Gly Asp Asn Phe Arg Thr Gln Lys Leu Ser Phe Ile Ile Arg Thr Val
785                 790                 795                 800

Gly Arg His Phe Pro Gly His Leu Leu Ala Trp Asp Phe Val Lys Glu
                805                 810                 815

Asn Trp Asn Lys Leu Val Gln Lys Phe Pro Leu Gly Ser Tyr Thr Ile
            820                 825                 830

Gln Asn Ile Val Ala Gly Ser Thr Tyr Leu Phe Ser Thr Lys Thr His
        835                 840                 845

Leu Ser Glu Val Gln Ala Phe Phe Glu Asn Gln Ser Glu Ala Thr Phe
    850                 855                 860

Arg Leu Arg Cys Val Gln Glu Ala Leu Glu Val Ile Gln Leu Asn Ile
865                 870                 875                 880

Gln Trp Met Glu Lys Asn Leu Lys Ser Leu Thr Trp Trp Leu
                885                 890
```

<210> SEQ ID NO 11
<211> LENGTH: 894
<212> TYPE: PRT
<213> ORGANISM: Homo sapiens
<220> FEATURE:
<221> NAME/KEY: PEPTIDE
<222> LOCATION: (1)..(894)

<400> SEQUENCE: 11

```
Pro Arg Cys Thr Phe Thr Lys Glu Gly Cys His Lys Lys Asn Gln Ser
1               5                   10                  15

Ile Gly Leu Ile Gln Pro Phe Ala Thr Asn Gly Lys Leu Phe Pro Trp
            20                  25                  30

Ala Gln Ile Arg Leu Pro Thr Ala Val Val Pro Leu Arg Tyr Glu Leu
        35                  40                  45

Ser Leu His Pro Asn Leu Thr Ser Met Thr Phe Arg Gly Ser Val Thr
    50                  55                  60

Ile Ser Val Gln Ala Leu Gln Val Thr Trp Asn Ile Ile Leu His Ser
65                  70                  75                  80

Thr Gly His Asn Ile Ser Arg Val Thr Phe Met Ser Ala Val Ser Ser
                85                  90                  95

Gln Glu Lys Gln Ala Glu Ile Leu Glu Tyr Ala Tyr His Gly Gln Ile
            100                 105                 110

Ala Ile Val Ala Pro Glu Ala Leu Leu Ala Gly His Asn Tyr Thr Leu
        115                 120                 125
```

-continued

```
Lys Ile Glu Tyr Ser Ala Asn Ile Ser Ser Tyr Gly Phe Tyr
    130                 135                 140
Gly Phe Ser Tyr Thr Asp Glu Ser Asn Glu Lys Lys Tyr Phe Ala Ala
145                 150                 155                 160
Thr Gln Phe Glu Pro Leu Ala Ala Arg Ser Ala Phe Pro Cys Phe Asp
                165                 170                 175
Glu Pro Ala Phe Lys Ala Thr Phe Ile Ile Lys Ile Ile Arg Asp Glu
            180                 185                 190
Gln Tyr Thr Ala Leu Ser Asn Met Pro Lys Lys Ser Ser Val Val Leu
        195                 200                 205
Asp Asp Gly Leu Val Gln Asp Glu Phe Ser Glu Ser Val Lys Met Ser
210                 215                 220
Thr Tyr Leu Val Ala Phe Ile Val Gly Glu Met Lys Asn Leu Ser Gln
225                 230                 235                 240
Asp Val Asn Gly Thr Leu Val Ser Ile Tyr Ala Val Pro Glu Lys Ile
                245                 250                 255
Gly Gln Val His Tyr Ala Leu Glu Thr Thr Val Lys Leu Leu Glu Phe
            260                 265                 270
Phe Gln Asn Tyr Phe Glu Ile Gln Tyr Pro Leu Lys Lys Leu Asp Leu
        275                 280                 285
Val Ala Ile Pro Asp Phe Glu Ala Gly Ala Met Glu Asn Trp Gly Leu
290                 295                 300
Leu Thr Phe Arg Glu Glu Thr Leu Leu Tyr Asp Ser Asn Thr Ser Ser
305                 310                 315                 320
Met Ala Asp Arg Lys Leu Val Thr Lys Ile Ile Ala His Glu Leu Ala
                325                 330                 335
His Gln Trp Phe Gly Asn Leu Val Thr Met Lys Trp Trp Asn Asp Leu
            340                 345                 350
Trp Leu Asn Glu Gly Phe Ala Thr Phe Met Glu Tyr Phe Ser Leu Glu
        355                 360                 365
Lys Ile Phe Lys Glu Leu Ser Ser Tyr Glu Asp Phe Leu Asp Ala Arg
370                 375                 380
Phe Lys Thr Met Lys Lys Asp Ser Leu Asn Ser Ser His Pro Ile Ser
385                 390                 395                 400
Ser Ser Val Gln Ser Ser Glu Gln Ile Glu Glu Met Phe Asp Ser Leu
                405                 410                 415
Ser Tyr Phe Lys Gly Ser Ser Leu Leu Leu Met Leu Lys Thr Tyr Leu
            420                 425                 430
Ser Glu Asp Val Phe Gln His Ala Val Val Leu Tyr Leu His Asn His
        435                 440                 445
Ser Tyr Ala Ser Ile Gln Ser Asp Asp Leu Trp Asp Ser Phe Asn Glu
450                 455                 460
Val Thr Asn Gln Thr Leu Asp Val Lys Arg Met Met Lys Thr Trp Thr
465                 470                 475                 480
Leu Gln Lys Gly Phe Pro Leu Val Thr Val Gln Lys Lys Gly Lys Glu
                485                 490                 495
Leu Phe Ile Gln Gln Glu Arg Phe Phe Leu Asn Met Lys Pro Glu Ile
            500                 505                 510
Gln Pro Ser Asp Thr Ser Tyr Leu Trp His Ile Pro Leu Ser Tyr Val
        515                 520                 525
Thr Glu Gly Arg Asn Tyr Ser Lys Tyr Gln Ser Val Ser Leu Leu Asp
530                 535                 540
Lys Lys Ser Gly Val Ile Asn Leu Thr Glu Glu Val Leu Trp Val Lys
```

```
545                 550                 555                 560

Val Asn Ile Asn Met Asn Gly Tyr Tyr Ile His Tyr Ala Asp Asp
                565                 570                 575

Asp Trp Glu Ala Leu Ile His Gln Leu Lys Ile Asn Pro Tyr Val Leu
                580                 585                 590

Ser Asp Lys Asp Arg Ala Asn Leu Ile Asn Asn Ile Phe Glu Leu Ala
                595                 600                 605

Gly Leu Gly Lys Val Pro Leu Lys Arg Ala Phe Asp Leu Ile Asn Tyr
                610                 615                 620

Leu Gly Asn Glu Asn His Thr Ala Pro Ile Thr Glu Ala Leu Phe Gln
625                 630                 635                 640

Thr Asp Leu Ile Tyr Asn Leu Leu Glu Lys Leu Gly Tyr Met Asp Leu
                645                 650                 655

Ala Ser Arg Leu Val Thr Arg Val Phe Lys Leu Leu Gln Asn Gln Ile
                660                 665                 670

Gln Gln Gln Thr Trp Thr Asp Glu Gly Thr Pro Ser Met Arg Glu Leu
                675                 680                 685

Arg Ser Ala Leu Leu Glu Phe Ala Cys Thr His Asn Leu Gly Asn Cys
                690                 695                 700

Ser Thr Thr Ala Met Lys Leu Phe Asp Asp Trp Met Ala Ser Asn Gly
705                 710                 715                 720

Thr Gln Ser Leu Pro Thr Asp Val Met Thr Thr Val Phe Lys Val Gly
                725                 730                 735

Ala Lys Thr Asp Lys Gly Trp Ser Phe Leu Leu Gly Lys Tyr Ile Ser
                740                 745                 750

Ile Gly Ser Glu Ala Glu Lys Asn Lys Ile Leu Glu Ala Leu Ala Ser
                755                 760                 765

Ser Glu Asp Val Arg Lys Leu Tyr Trp Leu Met Lys Ser Ser Leu Asn
                770                 775                 780

Gly Asp Asn Phe Arg Thr Gln Lys Leu Ser Phe Ile Ile Arg Thr Val
785                 790                 795                 800

Gly Arg His Phe Pro Gly His Leu Leu Ala Trp Asp Phe Val Lys Glu
                805                 810                 815

Asn Trp Asn Lys Leu Val Gln Lys Phe Pro Leu Gly Ser Tyr Thr Val
                820                 825                 830

Gln Asn Ile Val Ala Gly Ser Thr Tyr Leu Phe Ser Thr Lys Thr His
                835                 840                 845

Leu Ser Glu Val Gln Ala Phe Phe Glu Asn Gln Ser Glu Ala Thr Phe
                850                 855                 860

Arg Leu Arg Cys Val Gln Glu Ala Leu Glu Val Ile Gln Leu Asn Ile
865                 870                 875                 880

Gln Trp Met Glu Lys Asn Leu Lys Ser Leu Thr Trp Trp Leu
                885                 890
```

USE OF THE IRAP PROTEIN FOR IMPLEMENTING METHODS OF DIAGNOSIS AND OF PROGNOSIS

FIELD OF THE INVENTION

The invention relates to the use of the IRAP protein for implementing methods of diagnosis and of prognosis.

BACKGROUND OF THE INVENTION

The IRAP protein (Insulin-Regulated AminoPeptidase; EC 3.4.11.3) also known as Placental Leucine AminoPeptidase (P-LAP) and Leucine-cystinyl aminopeptidase (L-CAP) is a transmembrane zinc metalloproteinase protein which exists in three isoforms (Swiss-Prot: Q9UIQ6:1, 2 and 3; represented respectively by SEQ ID No: 1 to 3).

When it is inserted into the plasma membrane its extracellular domain can be cleaved and secreted.

The secreted part of an unspecified isoform of the protein assumed to be IRAP was assayed in the blood by an enzymatic method using a non-specific synthetic substrate, L-leucine-nitroanilide in the presence of methionine (Mizutani, S., Yoshino, M., and Oya, M. (1976) *Clin Biochem* 9(1), 16-18).

Using this method Mizutani, Oya and Tomoda detected a cystinyl-leucine aminopeptidase in the serum of pregnant women, the concentration of which increases during pregnancy (Yamahara, N., Nomura, S., Suzuki, T., Itakura, A., Ito, M., Okamoto, T., Tsujimoto, M., Nakazato, H., and Mizutani, S. (2000) *Life Sci* 66(15), 1401-1410). This aminopeptidase is essentially of placental origin, and therefore called P-LAP (Tsujimoto, M., Mizutani, S., Adachi, H., Kimura, M., Nakazato, H., and Tomoda, Y. (1992) *Arch Biochem Biophys* 292 (2), 388-392) and corresponds to the secreted domain of the protein.

This enzyme degrades oxytocin (Naruki, M., Mizutani, S., Goto, K., Tsujimoto, M., Nakazato, H., Itakura, A., Mizuno, K., Kurauchi, O., Kikkawa, F., and Tomoda, Y. (1996) *Peptides* 17(2), 257-261), vasopressin (Wallis, M. G., Lankford, M. F., and Keller, S. R. (2007) *Am J Physiol Endocrinol Metab* 293(4), E1092-1102), angiotensin II and III (Matsumoto, H., Rogi, T., Yamashiro, K., Kodama, S., Tsuruoka, N., Hattori, A., Takio, K., Mizutani, S., and Tsujimoto, M. (2000) *Eur J Biochem* 267(1), 46-52) as well as a series of other peptides (Albiston, A. L., Peck, G. R., Yeatman, H. R., Fernando, R., Ye, S., and Chai, S. Y. (2007) *Pharmacol Ther* 116(3), 417-427). The serous concentrations of this aminopeptidase have never been reported in men or non-pregnant women.

At the time of its cloning, it appeared that P-LAP corresponds to the IRAP protein as well as to the angiotensin IV receptor (Keller, S. R., Scott, H. M., Mastick, C. C., Aebersold, R., and Lienhard, G. E. (1995) *J Biol Chem* 270(40), 23612-23618; Rogi, T., Tsujimoto, M., Nakazato, H., Mizutani, S., and Tomoda, Y. (1996) *J Biol Chem* 271(1), 56-61; Albiston, A. L., McDowall, S. G., Matsacos, D., Sim, P., Clune, E., Mustafa, T., Lee, J., Mendelsohn, F. A., Simpson, R. J., Connolly, L. M., and Chai, S. Y. (2001) *J Biol Chem* 276(52), 48623-48626).

Patent Application WO 2005/038462 describes a reagent for diagnosis and/or prognostic evaluation of carcinoma, comprising an anti-P-LAP polyclonal antibody, obtained by immunization with the whole P-LAP protein. Given the strong homology between the different aminopeptidases, the antibody is probably not specific to IRAP and should also recognize other aminopeptidases. It should not therefore make it possible to diagnose a pathology linked in a precise manner to a modification of the expression or plasmatic concentration of IRAP.

GLUT4 is the glucose transporter which allows the uptake of circulating glucose by the muscles and the adipose tissue in response to insulin. Under unstimulated conditions (basal conditions), GLUT4 is effectively retained inside the cell in intracellular compartments (vesicles), by a still-unknown retention mechanism. In response to insulin stimulation, GLUT4 is transported then inserted into the plasma membrane by increased translocation, thus the allowing the cellular uptake of glucose.

IRAP co-localizes with the glucose transporter GLUT4 and is co-translocated with the latter stoichiometrically (Keller, S. R. (2004) *Biol Pharm Bull* 27(6), 761-764). This translocation towards the plasma membrane is stimulated by insulin in the same manner as that of GLUT4 (Karylowski, O., Zeigerer, A., Cohen, A., and McGraw, T. E. (2004) *Mol Biol Cell* 15(2), 870-882; Subtil, A., Lampson, M. A., Keller, S. R., and McGraw, T. E. (2000) *J Biol Chem* 275(7), 4787-4795).

Moreover, the expression of IRAP conditions the expression of GLUT4 as, in IRAP$^{-/-}$ transgenic animals, the GLUT4 levels are reduced by 50 to 80% (Keller, S. R., Davis, A. C., and Clairmont, K. B. (2002) *J Biol Chem* 277(20), 17677-17686).

In type 2 diabetics both a reduction of the expression and the translocation of GLUT4 towards the plasma membrane in the muscle and the adipose tissue is found (Kahn, B. B. (1992) *J Clin Invest* 89(5), 1367-1374).

Similarly and although the cellular levels of IRAP are not modified, its translocation is also reduced in the muscle and the adipose tissue of type 2 diabetics (Garvey, W. T., Maianu, L., Zhu, J. H., Brechtel-Hook, G., Wallace, P., and Baron, A. D. (1998) *J Clin Invest* 101(11), 2377-2386; Maianu, L., Keller, S. R., and Garvey, W. T. (2001) *J Clin Endocrinol Metab* 86(11), 5450-5456).

Moreover, a relationship has been demonstrated between the IRAP protein and the development of chemoresistance to anticancer drugs (Kondo C. et al., *Int J. Cancer*, 118, 1390-1394, 2006). According to this article, IRAP in fact reduces sensitivity to anticancer drugs by inhibiting the expression of the apoptosis-induction factor and increases expression of the apoptosis-inhibition factor.

The extracellular domain of IRAP is cleaved by metalloproteases probably belonging to the ADAM family including ADAM9 (SwissProt Q13443) and ADAM12 (SwissProt O43184) (Ito, N., Nomura, S., Iwase, A., Ito, T., Kikkawa, F., Tsujimoto, M., Ishiura, S., and Mizutani, S. (2004) *Biochem Biophys Res Commun* 314(4), 1008-1013) and released into the blood circulation. ADAM9 (MDC9) is expressed in different tissues including the skeletal muscle and adipose tissue (Hotoda, N., Koike, H., Sasagawa, N., and Ishiura, S. (2002) *Biochem Biophys Res Commun* 293(2), 800-805) and ADAM12 is essentially expressed in the muscle. Several other members of this family are also expressed in the muscle and adipose tissue.

At present, the only relationships described between the concentration of the extracellular domain of IRAP in a biological medium and a pathology concern severe preeclampsia as well as the risk of premature labour. In these two pathologies the circulating P-LAP concentrations are less than those observed in the control women of equivalent gestational age. However, the methods described in the prior art are based on the enzymatic assay, using a non-specific substrate, of the extracellular domain of IRAP.

There is therefore a real need to provide a reliable and specific method making it possible to assay the extracellular domain of circulating IRAP.

SUMMARY OF THE INVENTION

One of the purposes of the present invention is to provide an in vitro method for the assay of the concentration of IRAP protein in serum or plasma or tissues of a mammal, specifically of the extracellular domain of the IRAP protein.

Another purpose of the invention is to provide a monoclonal antibody specific to the extracellular domain of the different isoforms of the IRAP protein.

Another purpose of the invention is to provide a method for the diagnosis of pathologies in which an excess or a reduction of the IRAP protein concentration is involved.

A last purpose is to provide a monoclonal antibody specific to the extracellular domain of the different isoforms of the IRAP protein and inhibitor of their enzymatic activity from a therapeutic perspective.

As a result, the present invention relates to the use of the extracellular domain of the IRAP protein ("insulin-responsive aminopeptidase"), for implementing a method for the in vitro assay of the concentration of the secreted extracellular domain of the IRAP protein in serum, plasma or tissues of mammals, in particular of humans.

DETAILED DESCRIPTION OF THE INVENTION

The IRAP protein can have different names such as: "Insulin-responsive aminopeptidase", "Insulin-regulated membrane aminopeptidase", "Leucyl-cystinyl aminopeptidase (L-CAP)", "Placental leucine aminopeptidase (P-LAP)", "Cystinyl aminopeptidase", "Oxytocinase", "OTase", "Vesicle protein of 165 kDa", "Vp165", or "GP160". These all correspond to one or more of the isoforms of the protein registered under No. Q9UIQ6 1, 2 and 3 in the Swiss-Prot database.

These different names may be used interchangeably in the remainder of the description and denote the same protein.

The IRAP protein, whatever its isoforms, is constituted by an N-terminal part of approximately 110 amino acids present in the cytoplasm, by a transmembrane part of approximately 20 amino acids and an extracellular C-terminal part comprising the remaining amino acids.

As indicated above, the extracellular domain can be cleaved and secreted.

Consequently, the expression "extracellular domain" comprises both the extracellular domain still linked to the cell membrane and consequently found in the tissues, and the circulating extracellular domain, i.e. after cleavage and secretion, which is found in the blood circulation.

By "mammal" is meant a taxon included in the vertebrates which consists of approximately 5400 species. Said species are defined in: Wilson, D. E., and Reeder, D. M. (eds), *Mammal Species of the World*, Johns Hopkins University Press, 16 Nov. 2005.

One of the advantages of the in vitro assay method of the invention is therefore that of allowing the specific assay of the extracellular domain of the IRAP protein in a mammal and more particularly:
  either the extracellular domain circulating in the serum, or the plasma
  or the extracellular domain also linked to the membrane in the tissues, including the red blood cells.

In an advantageous embodiment, the invention relates to the use of the extracellular domain of the IRAP protein, in which said IRAP protein corresponds to one of its isoforms, in particular the isoforms defined by SEQ ID No. 1 to 3, or one of its variants, in particular the variants defined by the SEQ ID No. 4 to 6, said extracellular domain being represented by the SEQ ID No. 7 to 11.

The IRAP protein can exist in at least three isoforms (Swiss-Prot: Q9UIQ6 1, 2 and 3; represented by SEQ ID No. 1 to 3 respectively) as well as several variants of the isoform 1: 031616 (S86P, serine replaced by a proline in position 86), 012812 (A763T alanine replaced by a threonine in position 763) and 031617 (I963V; isoleucine replaced by a valine in position 963) represented by the SEQ ID No. 4 to 6 respectively.

The extracellular domain of each isoform 1 to 3 is represented by the SEQ ID No. 7 to 9 respectively and the extracellular domain of the variants 031616, 0128412 and 031617 is represented by the SEQ ID No. 7, 10 and 11.

Throughout this description, the term IRAP can be used alone but also includes its isoforms and/or variants.

In an advantageous embodiment, the invention relates to the use of the extracellular domain of the IRAP protein defined above and/or one of its isoforms defined above and/or one of its variants defined above, for the in vitro diagnosis and/or prognosis, or the in vitro monitoring of pathologies linked to translocation defects of the GLUT4 glucose transporter or of associated proteins, including IRAP.

By "in vitro diagnosis" is meant the reasoning leading to the in vitro identification of the cause (origin) of a failure, a problem or a disease.

By "in vitro prognosis" is meant the in vitro assessment of the degree of seriousness and subsequent development of a disease including its outcome.

As specified above, IRAP co-localizes with the GLUT4 glucose transporter and is co-translocated with the latter stoichiometrically.

Consequently, the determination of the concentration of the IRAP protein or one of its isoforms or one of its variants defined above present in the serum or the plasma, the red blood corpuscles or the tissues is representative of the translocation and therefore of the transport quantity of glucose.

Another advantage of the assay method of the invention is therefore the determination of a glucose transport defect and as a result the identification of the cause of a pathology or of its degree of seriousness or also the monitoring of the pathology and of its development.

In an advantageous embodiment, the assay method defined above allows the evaluation of a treatment directed against this disease by comparing the concentrations of the extracellular domain of IRAP protein obtained before and after the treatment.

The pathologies linked with a glucose transport defect may be, without being limited to these: insulin-resistance, type 2 diabetes, gestational diabetes. According to a more advantageous embodiment, the use of the extracellular domain of the IRAP protein defined above and/or one of its isoforms defined above and/or of one of its variants defined above, allows the in vitro diagnosis and/or prognosis of pathologies associated with the overexpression of IRAP at, and/or increase in the translocation to, the plasma membrane of IRAP and/or of its isoforms and/or variants compared with a healthy individual, or the in vitro monitoring of pathologies associated with the overexpression of IRAP and/or of its isoforms and/or variants in a patient, compared with a healthy individual.

In the context of an overexpression of IRAP at, and/or increase in the translocation of the IRAP protein to, the plasma membrane, the concentration of the extracellular domain of the IRAP protein, secreted or not, determined in a patient, by the assay method of the invention, is greater than that obtained in a healthy individual, thus indicating an overexpression of the IRAP protein.

In the context of the monitoring of a pathology linked to an overexpression of the IRAP protein at, and/or increase in the translocation of the IRAP protein to, the plasma membrane in a patient, the reduction in the concentration of the extracellular domain of the IRAP protein determined in said patient in the course of treatment by the assay method of the invention, compared with the concentration of the extracellular domain of the IRAP protein determined before treatment, makes it possible to demonstrate the efficacy of the treatment.

Conversely, an increase in or a stabilization of the concentration of the extracellular domain of the IRAP protein determined in said patient in the course of treatment, compared with the concentration of the extracellular domain, secreted or not, of the IRAP protein determined before treatment, shows the ineffectiveness of the treatment thus allowing a modification of the doses or of the active ingredient used.

As a result, it is considered that there is overexpression of the IRAP protein at, and/or an increase in the translocation of the IRAP protein to, the plasma membrane in an individual when the maximum value of the concentration of IRAP protein, secreted or not, indicated above is increased by 25% or more in a patient.

Examples of pathologies linked to the an overexpression of the IRAP protein at, and/or the increase in the translocation of the IRAP protein to, the plasma membrane, without being limited to these are all the diseases involving a proliferative phenomenon, in particular cancers, such as but not exhaustively: ovarian adenocarcinoma, endometrial cancer, choriocarcinoma, pancreatic cancer, breast cancer, prostate cancer, stomach cancer, rectal cancer or head and neck cancers.

According to a more advantageous embodiment, the use of the extracellular domain of the IRAP protein defined above and/or one of its isoforms defined above and/or one of its variants defined above, allows the in vitro diagnosis and/or prognosis of pathologies associated with the underexpression of IRAP at, and/or the reduction in the translocation to, the plasma membrane of IRAP and/or its isoforms and/or variants compared with a healthy individual, or the in vitro monitoring of pathologies associated with the underexpression of IRAP at, and/or reduction in the translocation to, the plasma membrane of IRAP and/or its isoforms and/or variants in a patient.

In the context of an underexpression of the IRAP protein at, and/or reduction in the translocation of the IRAP protein to, the plasma membrane, the concentration of the extracellular domain, secreted or not, of the IRAP protein determined in a patient, by the assay method of the invention, is less than that obtained in a healthy individual, thus indicating an underexpression of the IRAP protein at, and/or a reduction in the translocation of the IRAP protein to, the plasma membrane.

In the context of the monitoring of a pathology linked to an underexpression of the IRAP protein at, and/or a reduction in the translocation of the IRAP protein to, the plasma membrane in a patient, the increase in the concentration of the extracellular domain of the IRAP protein determined in said patient in the course of treatment by the assay method of the invention, compared with the concentration of the extracellular domain of the IRAP protein determined before treatment, makes it possible to demonstrate the efficacy of the treatment.

Conversely, a reduction in or a stabilization of the concentration of the extracellular domain of the IRAP protein determined in said patient in the course of treatment, compared with the concentration of the extracellular domain of the IRAP protein determined before treatment, shows the ineffectiveness of the treatment thus allowing a modification of the doses or of the active ingredient used.

It is considered that there is underexpression of the IRAP protein when the minimum value of the concentration of IRAP protein indicated above is reduced by 25% or more.

In an advantageous embodiment, the use of the extracellular domain of the IRAP protein defined above, and/or of one of its isoforms defined above and/or of one of its variants defined above, allows the in vitro diagnosis and/or prognosis of chemoresistance to anticancer drugs.

By the term "chemoresistance", is meant a reduced or a complete loss of sensitivity to anticancer treatment during chemotherapy with anticancer drugs, which is acquired or inherent, and which restricts or completely destroys the efficacy of the anticancer treatment.

Examples of anticancer drugs, without being limited to these, are paclitaxel (Taxol), carboplatin etc.

As a result, the assay of the extracellular domain of IRAP and/or of one of its isoforms defined above, and/or of one of its variants defined above, exhibiting an overexpression of the IRAP protein at, and/or an increase in the translocation of the IRAP protein to, the plasma membrane in an individual, in particular when the maximum value of the concentration of IRAP protein indicated above is increased by 25% or more in a patient, allows the diagnosis and/or the prognosis of the resistance to the chemotherapy.

According to an advantageous embodiment, the use of the extracellular domain of the IRAP protein defined above and/or of one of its isoforms defined above, and/or of one of its variants defined above, allows the in vitro diagnosis and/or prognosis, or the in vitro monitoring of pathologies linked to translocation defects of the GLUT4 glucose transporter and in particular to the underexpression of IRAP and/or of its isoforms and/or variants, which are among those associated with insulin resistance, type 2 diabetes, gestational diabetes.

Insulin-resistance leads to a less satisfactory uptake of glucose by the sensitive tissues in response to insulin. This disease develops into type 2 diabetes which appears when the glucose level in the blood (glycaemia) exceeds normal values (110 mg/dL fasting and 140 mg/dL 2 h after the ingestion of 75 g of glucose). This increase in the glucose level in the blood hyper-stimulates the pancreas, which increases the secretion of insulin in order to compensate for the increase in glycaemia.

Gestational diabetes represents any state of glucose intolerance, irrespective of its severity, appearing during pregnancy in a woman not previously known to have sugar diabetes.

Preeclampsia is a disease characterized by the association of arterial hypertension, proteinuria, and weight gain with oedema.

The risk of premature labour is characterized by uterine contractions resulting in shortening and opening of the cervix which can cause labour before the end of the $36^{th}$ week of pregnancy.

Consequently, another advantage of the invention is allowing the in vitro diagnosis and/or prognosis, or the in vitro monitoring of pathologies linked to translocation defects of the GLUT4 glucose transporter both in the tissues and in the serum, plasma or red blood corpuscles.

According to another advantageous embodiment, the use of the extracellular domain of the IRAP protein defined above and/or of one of its isoforms defined above, and/or of one of its variants defined above, allows the in vitro diagnosis and/or prognosis, or the in vitro monitoring of pathologies linked to translocation defects of the GLUT4 glucose transporter, in particular cancers, in particular those in which IRAP and/or its isoforms and/or variants are overexpressed such as ovarian adenocarcinoma, endometrial cancer, choriocarcinoma, pancreatic cancer, breast cancer, prostate cancer, stomach cancer, rectal cancer or head and neck cancers, auto-immune or inflammatory diseases.

Choriocarcinoma is a highly malignant tumour constituted by the juxtaposition of cytotrophoblast and syncytiotrophoblast cellular elements with complete disappearance of the chorionic villi.

In an advantageous embodiment, the detection of the cancers mentioned in the document WO 2005/038462 by the method of the invention is carried out in the serum, and also in the plasma or on the red blood corpuscles.

By auto-immune disease is meant diseases due to hyperactivity of the immune system vis-à-vis substances or tissues which are normally present in the organism, such as auto-immune thyroiditis, rheumatoid arthritis, ankylosing spondylitis, Gougerot-Sjögren's syndrome.

Examples of inflammatory diseases, but without being limited to these, are the following:

rheumatoid arthritis, lupus erythematosus, Sjögren's syndrome, scleroderma (systemic sclerosis), dermatomyositis, polymyositis, polymyalgia rheumatica, osteoarthritis, septic arthritis, gout, pseudogout, spondylarthropathy, ankylosing spondylitis, Reiter's syndrome, psoriatic arthropathy, enteropathic spondylitis, reactive arthropathy, Crohn's disease, sarcoidosis etc.

In the context of treatment with an anticancer drug, IRAP reduces sensitivity to these medicaments by inhibiting expression of the apoptosis promoting factor and by increasing expression of the apoptosis inhibiting factor (Kondo et al., Int. J. Cancer: 118, 1390-1394, 2006).

According to a more advantageous embodiment, the implementation of an in vitro assay method by means of the extracellular domain of the IRAP protein defined above and/or one of its isoforms defined above, and/or one of its variants defined above is carried out using an antibody.

The term "antibody" is used to denote polyclonal or monoclonal antibodies specific to the extracellular domain of one of the isoforms of the IRAP protein and also comprises fragments or molecules which mimic the monoclonal antibodies specific to the extracellular domain of the IRAP protein, and in particular a fragment binding to an epitope.

Fragments or molecules can be derived from monoclonal antibodies by recombinant DNA techniques or by enzymatic or chemical methods and can have binding characteristics similar to a those of a monoclonal antibody for an antigen fragment.

The antibodies of the present invention comprise both the full length of the antibodies discussed above, as well as fragments of those binding to epitopes. As it is used hereafter, the expression "antibody fragments" comprises any part of an antibody which retains the ability to bind to an epitope recognized by the full length of the antibody, generally called "fragments binding to an epitope".

Examples of antibody fragments include, but are not limited to: Fab, Fab' and F(ab')$_2$, Fd, single-chain Fvs (scFv), single-chain antibodies, Fvs linked by disulphide bridges and fragments comprising either a VL or VH region. Fragments binding to an epitope, including single-chain antibodies, can comprise the variable region(s) alone or in combination with all or part of the following elements: hinge region, the CH1, CH2, and CH3 domains.

These fragments can contain one or both Fab fragments or the F(ab')$_2$ fragment. Moreover, the fragments can be or can combine the members of any one of the following immunoglobulin categories: IgG, IgM, IgA, IgD, or IgE, and the sub-classes thereof.

Fab and F(ab')$_2$ fragments can be produced by proteolytic cleavage, using enzymes such as papain (Fab fragments) or pepsin (F(ab')$_2$ fragments).

The antibodies of the invention can be produced using conventional methods, comprising the immunization of an animal and the recovery of the spleen cells in order to produce hybridomas by cell fusion. The antibodies of the invention can be used advantageously in the form of a mixture of monoclonal antibodies.

According to an advantageous embodiment, said antibody defined above is a polyclonal antibody.

By "polyclonal antibody" is meant an antibody originating from different B lymphocyte cell lines.

In an advantageous embodiment, said polyclonal antibody defined above is used for implementing a method for the in vitro assay of the concentration of the IRAP protein defined above and/or one of its isoforms defined above, and/or variants in serum, plasma or red blood corpuscles from a mammal, in particular from a human within the context of insulin-resistance or cancer, or in tissues from a mammal within the context of insulin-resistance.

According to another advantageous embodiment, said antibody defined above is a monoclonal antibody.

By "monoclonal antibody" is meant an antibody originating from a single cell clone, i.e. a hybridoma.

In an advantageous embodiment, said monoclonal antibody defined above is used for implementing a method for the in vitro assay of the concentration of the IRAP protein defined above and/or one of its isoforms defined above and/or one of its variants, in serum, plasma, red blood corpuscles or tissues from a mammal, in particular a human, within the context of insulin-resistance or cancer.

According to an advantageous embodiment, the monoclonal antibody as defined above is produced by a hybridoma.

By "hybridoma" is meant a fusion cell which continuously produces antibodies, i.e. tumour cells which can reproduce indefinitely and which are fused with cells from mammals.

According to another aspect, the invention relates to an antibody specifically recognizing the circulating extracellular domain, or one of the epitopes of the extracellular domain, of the IRAP (insulin-responsive aminopeptidase) protein and/or one of its isoforms, in particular the isoforms defined by SEQ ID No. 1 to 3, and/or one of its variants, in particular the variants defined by SEQ ID No. 4 to 6, said extracellular domain being defined by the sequences SEQ ID No. 7 to 11.

One of the advantages of the invention is therefore to provide an antibody specific to the extracellular domain or one of the epitopes of the IRAP protein and/or one of its isoforms and/or one of its variants, i.e. specifically recognizing said extracellular domain or one of its epitopes, whether the extracellular domain is still linked to the plasma membrane of the cell or has been cleaved by metalloproteases belonging or not belonging to the ADAM family, in particular ADAM9 and ADAM12, and is therefore circulating and which does not recognize the transmembrane part or the intracellular part.

As a result, the antibody of the invention specifically recognizes said extracellular domain or one of its epitopes, after co-translocation with GLUT4 transporter, and therefore allows a method for the in vitro diagnosis and/or prognosis, or in vitro monitoring of pathologies linked to defects in the translocation of GLUT4 glucose transporter or associated proteins.

In an advantageous embodiment, the antibody defined above is used as medicament, in particular for the treatment of proliferative syndromes and cancers, in particular those in which IRAP and/or its isoforms and/or variants are overexpressed and/or the translocation of which towards the plasma membrane is increased, such as ovarian adenocarcinoma, endometrial cancer, choriocarcinoma, pancreatic cancer, breast cancer, prostate cancer, stomach cancer, rectal cancer or head and neck cancers, auto-immune or inflammatory diseases, or for the treatment of resistance to chemotherapy.

Reduction in the expression of IRAP at, and/or in its translocation towards the plasma membrane, i.e. return to a concentration in the serum or tissues which is close to normal, i.e. before the appearance of the cancer pathology or the partial or total inhibition of its activity with the antibodies of the invention therefore allows the treatment of cancers.

Similarly, as the IRAP protein is involved in reducing sensitivity to anticancer drugs as indicated above, the antibodies of the invention therefore make it possible to reduce the concentration of IRAP or to partially or totally inhibit its activity and/or its translocation towards the plasma membrane and therefore to dispense with reducing sensitivity to anticancer drugs leading to the treatment of resistance to chemotherapy and consequently to improvement of the efficacy of the anticancer drugs.

According to an advantageous embodiment, the antibody defined above is a polyclonal antibody.

According to an advantageous embodiment, the antibody defined above is a monoclonal antibody.

Another advantageous embodiment of the invention relates to a monoclonal antibody as defined above, said monoclonal antibody being chosen from:
  the monoclonal antibody secreted by the hybridoma deposited at the CNCM (Collection Nationale de Culture de Microorganismes, Institut Pasteur, Paris, France) on 2 Jul. 2009, under accession number CNCM I-4181,
  the monoclonal antibody secreted by the hybridoma deposited at the CNCM on 2 Jul. 2009, under accession number CNCM I-4182,
  the monoclonal antibody secreted by the hybridoma deposited at the CNCM on 2 Jul. 2009, under accession number CNCM I-4183,
  the monoclonal antibody secreted by the hybridoma deposited at the CNCM on 2 Jul. 2009, under accession number CNCM I-4184, and
  the monoclonal antibody secreted by the hybridoma deposited at the CNCM on 2 Jul. 2009, under accession number CNCM I-4185.

Hereafter, the monoclonal antibody No. CNCM I-4181 is also called antibody 17H10-3H5-3D8, or antibody 17H10, the monoclonal antibody No. CNCM I-4182 is also called antibody 14A4-3H9-2B6, or antibody 14A4, the monoclonal antibody No. CNCM I-4183 is also called antibody 4G6-3B6, or antibody 4G6, the monoclonal antibody No. CNCM I-4184 is also called antibody 38E1-2G4-3A2, or antibody 38E1, and the monoclonal antibody No. CNCM I-4185 is also called antibody 40C10-2G8, or antibody 40C10.

According to an advantageous embodiment, the monoclonal antibody is labelled with a compound chosen from a radionuclide, a fluorophore, a quantum dot, an enzyme label, an enzyme substrate, an enzyme cofactor, an enzyme inhibitor or a hapten.

The particular label or the detectable group used in the test is generally not a critical aspect of the invention, insofar as it does not interfere with the specific binding of the antibody used in the assay. The detectable group can be any material having a detectable physical or chemical property. Such detectable labels have been well developed in the field of immunological assays and, in general, almost any label which is useful in such methods can be applied to the method of the present invention.

Thus, a label is any composition which is detectable by spectroscopic, photochemical, biochemical, immunochemical, electrical, optical, radiological techniques or chemical means. Labels which are useful in the present invention include, but are not limited to: magnetic beads (for example Dynabeads™), fluorescent dyes (for example, fluorescein isothiocyanate, Texas red, rhodamine), radiolabelled labels (for example, $^3$H, $^{125}$I, $^{35}$S, $^{14}$C, or $^{32}$P), enzymes (for example horseradish peroxidase, alkaline phosphatase and others commonly used in an ELISA test), and colorimetric labels such as colloidal gold, coloured glass or plastic beads (for example polystyrene, polypropylene, latex, etc) and quantum dots.

The label can be coupled directly or indirectly to the desired test element according to methods well known in the art. As indicated above, a wide variety of labels can be used, the choice of the label depending on the necessary sensitivity, the ease of conjugation with the compound, stability requirements, available instrumentation and elimination conditions. Radioactive labels are often attached by indirect means.

As a general rule, a ligand molecule (for example biotin) is covalently bound to the antibody. The ligand then binds to an anti-ligand (for example streptavidin) molecule which is either inherently detectable or covalently bound to a signal system, such as a detectable enzyme, a fluorescent compound, or a chemiluminescent compound. A certain number of ligands and anti-ligands can be used. When a ligand has a naturally occurring anti-ligand, for example, biotin, thyroxine, and cortisol, it can be used in combination with the labelled, naturally occurring anti-ligand. Alternatively, a haptenic or antigenic compound can be used in combination with an antibody.

The antibody can also be conjugated directly to signal-generating compounds, e.g., by conjugation with an enzyme or fluorophore. Enzymes of interest, used as labels are mainly hydrolases, in particular phosphatases, esterases and glycosidases, or oxidoreductases, in particular peroxidases.

Fluorescent compounds include fluorescein and its derivatives, rhodamine and its derivatives, dansyl, umbelliferone, etc. Chemiluminescent compounds include luciferin, and 2,3-dihydrophthalazinediones, for example luminol and quantum dots. A review of labels or other signal-producing systems is available in U.S. Pat. No. 4,391,904.

Means for detecting labels are well known in the art. Thus, for example, when the label is a radioactive label, means for detection include a γ or β scintillation counter or photographic films as for autoradiography. When the label is a fluorescent label, it can be detected by exciting the fluorochrome with the appropriate light or laser wavelengths and detecting the resulting fluorescence. The fluorescence can be detected visually, by means of photographic film, by the use of electronic detectors such as charge coupled devices (CCDs) or photomultipliers and the like.

Similarly, enzymatic labels can be detected by providing the appropriate substrates for the enzyme and detecting the resulting reaction product. Finally, simple colorimetric labels can be detected directly by observing the colour associated with the label.

According to an advantageous embodiment, said monoclonal antibody defined above is a humanized antibody.

By "humanized antibody" is meant a genetically modified antibody in which the minimum part of a mouse antibody is incorporated in a human antibody; generally the humanized antibodies comprise 5-10% mouse antibody and of 90 to 95% human antibody.

The humanized antibodies have the advantage of blocking the HAMA (human anti-mouse antibody) and HACA (human anti-chimeric antibody) responses observed with the use of mouse or chimeric antibodies and which exhibit only a minimal response or no response of the human immune system to them.

According to another aspect, the invention relates to a hybridoma producing a monoclonal antibody as defined above.

Another advantageous aspect of the invention relates to a hybridoma as defined previously, said hybridoma being chosen from:
- the hybridoma deposited at the CNCM on 2 Jul. 2009, under accession number CNCM I-4181,
- the hybridoma deposited at the CNCM on 2 Jul. 2009, under accession number CNCM I-4182,
- the hybridoma deposited at the CNCM on 2 Jul. 2009, under accession number CNCM I-4183,
- the hybridoma deposited at the CNCM on 2 Jul. 2009, under accession number CNCM I-4184, and
- the hybridoma deposited at the CNCM on 2 Jul. 2009, under accession number CNCM I-4185.

The production of these hybridomas is described in the examples.

According to another aspect, the invention relates to a method for the in vitro assay of the concentration of IRAP protein, and/or one of its isoforms, and/or one of its variants in a mammal, comprising a stage of determination of the concentration of the extracellular domain of the IRAP protein and/or one of its isoforms and/or one of its variants in serum, plasma, the red blood corpuscles or tissues of a mammal.

The method of the invention therefore allows the specific assay of the extracellular domain of the IRAP protein after co-translocation with the GLUT4 glucose transporter and therefore makes it possible to determine the overexpression or the underexpression and/or the increase or reduction in the translocation of the IRAP protein and/or one of its isoforms and/or one of its variants responsible for associated pathologies.

Assay method according to claim 18, in which the assay is carried out either by an immuno-enzymatic method or by an immuno-histochemical method, or by RIA or IRMA.

The assay of the extracellular domain of the IRAP protein can be carried out either by immuno-enzymatic assay (Example 3), or by immuno-histochemical assay (Example 4), RIA (radio immuno-assay) or IRMA (immunoradiometric assay). In the latter case, the assay is carried out using either antibodies or protein or a fragment of the latter, labelled with iodine 125 or with any other appropriate radioisotope.

According to another aspect, the invention relates to a method for the in vitro diagnosis of pathologies associated with insulin resistance as well as type 2 diabetes, gestational diabetes, pregnancy-induced hypertension (preeclampsia), the risk of premature labour and comprising the following stages:
a. the in vitro determination of the concentration of circulating extracellular domain of the IRAP protein, i.e. also expressed at the plasma membrane of the red blood corpuscles, and/or one of its isoforms, and/or one of its variants, in a mammal using an antibody as defined above,
b. comparison of said concentration obtained in stage a. with that obtained in vitro in a healthy mammal,
c. deduction from the previous stage b., of the fact that the mammal has insulin-resistance, if the concentration obtained in stage a. is less than that of stage b., Another advantage of the invention is therefore to provide a method for the in vitro diagnosis and/or prognosis, or the in vitro monitoring of pathologies in which the IRAP protein and/or one of its isoforms and/or one of its variants is underexpressed.

According to another aspect, the present invention relates to a method for the in vitro diagnosis of pathologies associated with proliferative syndromes including cancers, in particular those in which IRAP, and/or one of its isoforms and/or one of its variants, is overexpressed or the translocation of which to the plasma membrane is increased, such as ovarian adenocarcinoma, or autoimmune or inflammatory diseases, or resistance to chemotherapy and comprising the following stages:
a. the in vitro determination of the concentration of circulating extracellular domain of the IRAP protein i.e. also expressed at the plasma membrane of the red blood corpuscles and/or one of its isoforms and/or one of its variants in a mammal, using an antibody as defined above,
b. comparison of said concentration obtained in stage a. with that obtained in vitro in a control mammal,
c. deduction from the previous stage b. of the fact that the mammal has a cancer, if the concentration obtained in stage a. is greater than that of stage b.

Another advantage of the invention is therefore to provide a method for the in vitro diagnosis and/or prognosis, or the in vitro monitoring of pathologies in which the IRAP protein and/or one of its isoforms and/or one of its variants is overexpressed, or the translocation of which to the plasma membrane is increased.

According to yet another aspect, the present invention relates to a kit for the in vitro determination of the concentration of circulating extracellular domain of the IRAP protein and/or one of its isoforms and/or variants in a mammal, comprising at least one buffer, and at least one antibody as defined above.

In a preferred embodiment, the kit defined above also comprises a substrate of the IRAP protein as well as a peptide or a fragment of IRAP recognized by the antibody.

Examples of substrate, without being limited to these are L-leucine-nitroanilide, vasopressin, oxytocin, the met-enkephalins etc.

By "peptide recognized by the antibody" is meant the recombinant IRAP protein or a fragment of the latter recognized by the antibody.

According to another aspect, the present invention relates to a method for the in vitro diagnosis of pathologies associated with cancers, in particular those in which IRAP and/or one of its isoforms and/or one of its variants is overexpressed, or the translocation of which to the plasma membrane is increased, such as ovarian adenocarcinoma, or with autoimmune or inflammatory diseases, or with resistance to chemotherapy and comprising the following stages:
a. the in vitro determination of the concentration of circulating extracellular domain of the IRAP protein, and/or one of its isoforms and/or one of its variants in a mammal using at least one monoclonal antibody as defined above, preferentially 2 monoclonal antibodies as defined above, in particular the antibodies 17H10 and 4G6 or 40C10,
b. comparison of said concentration obtained in stage a. with that obtained in vitro in a control mammal,
c. deduction from the previous stage b. of the fact that the mammal has a cancer, if the concentration obtained in stage a. is greater than that of stage b.

According to another aspect, the invention relates to a method for the in vitro diagnosis of pathologies associated with insulin-resistance as well as type 2 diabetes, gestational diabetes, pregnancy-induced hypertension (preeclampsia), the risk of premature labour and comprising the following stages:
  a. the in vitro determination of the concentration of circulating extracellular domain of the IRAP protein, and/or one of its isoforms and/or one of its variants in a mammal using at least one monoclonal antibody as defined above, preferentially 2 monoclonal antibodies as defined above, in particular the antibodies 17H10 and 4G6 or 40C10,
  b. comparison of said concentration obtained in stage a. with that obtained in vitro in a healthy mammal,
  c. deduction from the previous stage b. of the fact that the mammal has insulin-resistance, if the concentration obtained in stage a. is less than that of stage b.

The following figures and examples illustrate the invention better, without however limiting its scope.

BRIEF DESCRIPTION OF THE DRAWINGS

FIG. 1A shows a graph measuring the detection of the IRAP protein (■) or IRAP His (♦) as a function of the concentration of the antibody 4G6.

FIG. 1B shows a graph measuring the detection of the IRAP protein (▲) or IRAP His (X) as a function of the concentration of the antibody 14H4.

FIG. 1C shows a graph measuring the detection of the IRAP protein (●) or IRAP His (*) as a function of the concentration of the antibody 17H10.

FIG. 1D shows a graph measuring the detection of the IRAP protein (+) or IRAP His (-) as a function of the concentration of the antibody 38E1.

FIG. 1E shows a graph measuring the detection of the IRAP protein (♦) or IRAP His (-) as a function of the concentration of the antibody 40C10.

EXAMPLES

Example 1

Production of the IRAP Protein

Figure 1A:
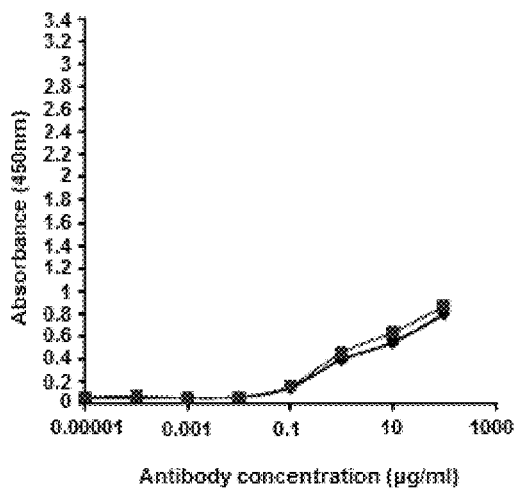
FIGS. 1A-E represent graphs corresponding to the measurement of the affinity of monoclonal antibodies 17H10, 14A4, 4G6, 38E1, 40C10 for the IRAP protein.
Figure 1B:
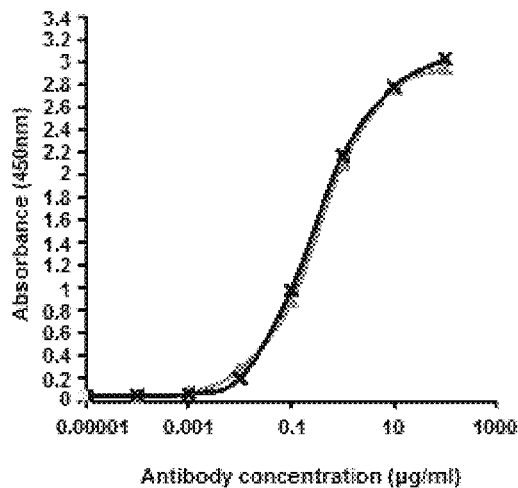
Figure 1C:
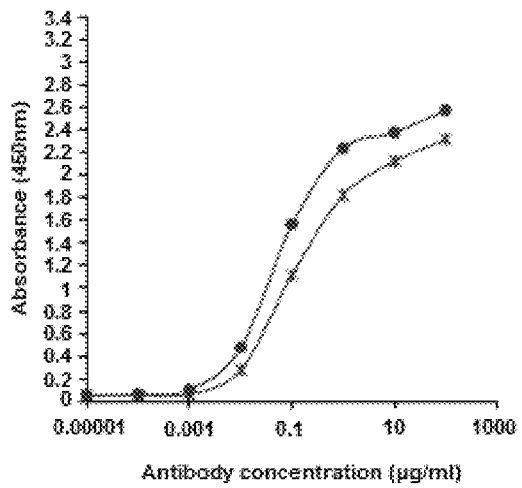
Figure 1D:
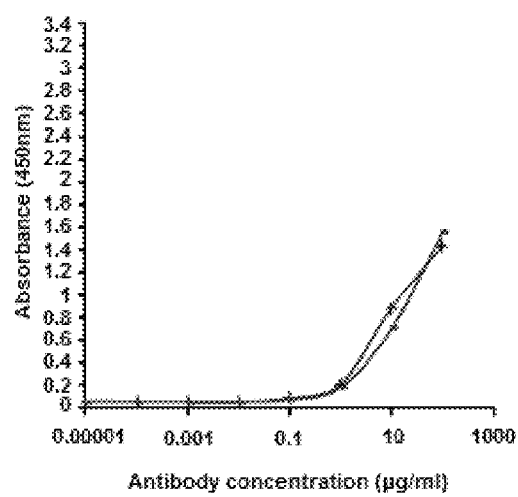
Figure 1E:
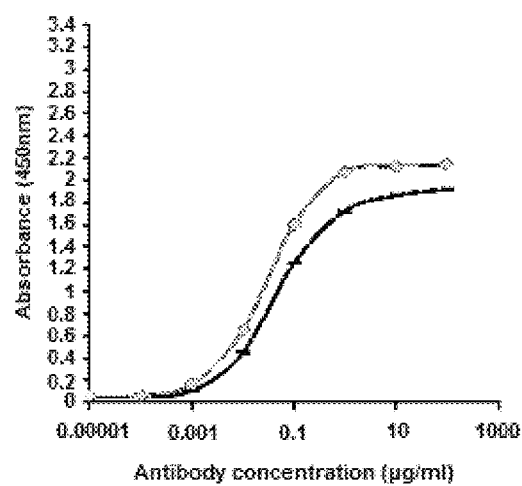

1. Cloning:
An expression vector containing the sequence coding for the extracellular domain of IRAP fused with an insect peptide signal and a 6 histidine tag cleavable by TEV protease at the N-terminal was constructed and its conformity with the sequence in the Swiss-Prot data base (Q9UIQ6) was verified by sequencing (pGTPb302-mel-His-Tev-PLAPextra, reference C640-CAP-06).

A recombinant bacmid was produced and the presence of the expression cassette in the bacmid generated was checked by PCR.

The recombinant virus was generated by transfection of the bacmid in the Sf9 insect cell line.

After a viral amplification, the second generation virus was assayed and used for a series of expression trials in insect/baculovirus cell systems.

2. Expression and purification of the circulating extracellular sequence of IRAP or one of its isoforms or one of its variants. Three different methods can be used:
  1st method: expression of the IRAP protein or one of its isoforms by an appropriate strain of *E. coli*. The IRAP protein or one of its secreted isoforms is then purified by affinity on an $Ni^{++}$ or $Co^{++}$ matrix.
  Finally, the poly-His sequences are cleaved using a specific protease.
  2nd method: expression of the IRAP protein or one of its isoforms or one of its variants by Sf9 insect cells after cloning of the modified cDNA in Baculovirus: The expression trials were carried out on 2 cell lines: Sf9 and HighFive by varying the MOI (multiplicity of infection) as well as the duration of infection. The analysis of the expression trials was carried out by anti His Western Blot on samples of culture supernatant taken at 24, 48 and 72 hours of infection and the most productive condition is at 48 hours of infection (HighFive MOI 0.1)
  The IRAP protein or one of its isoforms or one of its secreted variants is then purified by affinity on an $Ni^{++}$ or $Co^{++}$ matrix. Finally, the poly-His sequences are cleaved using a specific protease.

Example 2

Production of the Monoclonal Antibodies

General Point
The protocol originates from the hybridoma technique (Köhler and Milstein protocol, 1976) and is divided into 5 stages:
  Stage 1—Immunization: sub-cutaneous injection into mice of several peptides corresponding to specific sequences common to the extracellular part of the isoforms of IRAP or one of its variants. These peptide sequences are not found in the other aminopeptidases of mammals.
  The antisera are tested against the purified recombinant IRAP protein or one of its isoforms by ELISA. The spleens of the mice which respond are used for the generation of hybridomas. The antibodies produced by the latter are then retested by ELISA against the IRAP protein or one of its isoforms and the serum of pregnant and non-pregnant women.
  Stage 2—Fusion: taking the spleen cells and fusing these cells with myeloma cells in the presence of polyethylene glycol (chemical fusion agent). Distribution of the mixture into microplate wells at a dilution such that on average each well contains less than one hybrid cell. Culture of the cells in a selective medium where only the hybrid cells multiply and survive, while the myelomatous cells and the unfused plasmocytes of the spleen die rapidly.

Stage 3—Screening: seeking, in each well, antibodies directed against the IRAP protein or one of its isoforms or one of its recombinant variants.

Stage 4—Cloning and characterization: subculture of the hybrid cells producing antibodies in order to obtain cell clones. Storing of a copy of each clone in nitrogen liquid. Isotyping of the antibodies produced.

Stage 5—Culture and production: two possible methods for culturing the hybridomas in order to produce the anti-IRAP antibody or one of its isoforms or one of its variants:

in vitro culture of the cells (production of the antibodies in the culture medium)

in vivo culture by injection of the cells into the peritoneal cavity of mice. This causes the appearance of a tumour, inflammation and production of ascitic fluid in the injection zone. Sampling of the ascitic fluid which contains the antibody (1 to 10 mg/mL).

Specific Hybridomas

1—Immunization 6 female OF1 Charles River mice (18-20 g) were immunized by intravenous and sub-cutaneous injection with a mixture of peptides SEQ ID No. 7 to 11, the 5 peptides being coupled to KLH (Keyhole limpet hemocyanin) in the presence of Freund's complete adjuvant. 3 mice (mice 1 to 3) received 50 µg of the mixture of the peptides and 2 mice (mice 4 and 5) received 15 µg of the mixture of the peptides.

3 weeks after the first injection, the mice were reinjected with the mixture of the two peptides in the presence of Freund's incomplete adjuvant ($1^{st}$ booster).

3 weeks after the second injection, the mice were reinjected with the mixture of the two peptides in the presence of Freund's incomplete adjuvant (second booster).

1 month after the first injection, samples of serum of the injected mice were taken, and said sera were tested for the presence of antibody directed against the peptides SEQ ID No. 7 to 11.

The sera from all the mice had antibodies recognizing at least one of the peptides and were therefore stored.

10 days after the serum test, 3 mice received an intraperitoneal and intravenous booster of 20 µg of the mixture of the peptides. The spleens were removed 3 days after the booster.

1 month after the serum test, the 3 remaining mice received an intra-peritoneal and intravenous booster of 15 µg of the mixture of the peptides. The spleens were removed 3 days after the booster.

2—Cell Fusion

The mice were bled and their spleens were removed in a sterile fashion with DMEM. The spleens were ground and filtered through a grid.

In parallel, the intraperitoneal cavity of the mice was washed with DMEM, and the DMEM comprising the macrophages was recovered. The macrophages were counted in a Malassez cell in order to prepare a solution with 104 macrophages/ml in the following medium: DMEM HAT 20% FCS ATB (DMEM, 4 mM glutamine, HAT (hypoxantine 100 µM, aminopterin 0.4 µM, thymidine 16 µM), 20% decomplemented foetal calf serum, 1% antibiotics (Penicillin/Streptomycin)).

The splenocytes obtained were then washed three times with DMEM.

In parallel, myeloma cells from BalB/c Sp2/0 Ag14 mice (ATCC No. CRL 1581) are also washed 3 times in DMEM The splenocytes and the myeloma cells were mixed with a splenocytes/myeloma ratio of 5/1 and centrifuged at 244 g for 7 minutes.

The supernatant was removed and 1 ml of PEG (40% solution of polyethylene glycol, MW 1500 heated to 37° C.) was added.

The cells were centrifuged at 800 rpm (108 g) for 12 minutes, 10 ml of the following medium DMEM HAT 20% FCS (DMEM, 4 mM glutamine, HAT (hypoxantine 100 µM, aminopterin 0.4 µM, thymidine 16 µM), 20% decomplemented foetal calf serum) was added slowly.

The cells were centrifuged at 1200 rpm (244 g) for 7 minutes, the supernatant was removed and a volume v of DMEM HAT 20% FCS medium was added to the pellet such that:

$v$ (in ml)=no. of splenocytes/107 (i.e. 107 cells/ml)

The tube was left at ambient temperature for 1 hour before being turned carefully in order to resuspend the cells.

100 µl/well of the solution with 104 macrophages/ml was added to 96-well plates then 100 µl per well of fused cells was added at the following dilutions:

dilution 1/10: 3 plates with 105 splenocytes per well dilution 1/20: 5 plates (2×50 ml) with 5×104 splenocytes per well dilution 1/40: 2 plates with 2.5×104 splenocytes per well The plates were placed in an oven at 37° C., 5% CO2 for 10 days.

3—Selection of Hybridomas

After culture of the fusion products for 10 days two selection tests are carried out:

Test 1: The wells in which the cells have reached confluence are analyzed:

for the fusions originating from the splenocytes of the 3 first mice, 1017 wells were analyzed, for the fusions originating from the splenocytes of the 3 last mice, 714 wells were analyzed.

100 µl of supernatant was taken from each of these wells and the supernatants were tested using an ELISA test in order to detect antibodies directed against one or more peptides SEQ ID No. 7 to 11 (cf. Screening of the supernatants of the anti-TRAP hybridomas).

After the ELISA test, the selected cells (secreting antibodies directed against one or more peptides SEQ ID No. 7 to 11) were placed in 0.4 ml of medium in the wells of a 24-well plate.

When the cells began to multiply (24 to 48 hours), 1 ml of the medium: 15% DMEM HAT FCS 1% HCF ATB (DMEM, 4 mM glutamine, HAT (hypoxantine 100 µM, aminopterin 0.4 µM, thymidine 16 µM), 15% decomplemented foetal calf serum, 1% HCF (hybridoma cloning factor macrophage-like origin), 1% antibiotic (Penicillin/Streptomycin)) was added.

111 clones were selected and frozen in this way

Test 2: The wells in which the cells originating from the 111 clones selected by test 1 have reached confluence were analyzed:

for the fusions originating from the splenocytes of the 3 first mice, 39 wells of 24-well plates were analyzed, for the fusions originating from the splenocytes of the 3 last mice, 72 wells of 24-well plates were analyzed.

100 µl of supernatant was taken from each of these wells and the supernatants were tested using an ELISA test in order to detect antibodies directed against the secreted domain of IRAP (cf. Screening of the supernatants of the anti-IRAP hybridomas).

23 clones were selected and frozen in this way.

4—Screening of the Supernatants of the Anti-IRAP Hybridomas

Antigens (Ag) used: KLH-peptides SEQ ID No. 7 to 11 (first screening) and secreted domain of recombinant IRAP expressed in High Five insect cells (second screening).

| STAGES | CONDITIONS |
|---|---|
| Coating (adsorption of the Ag.) | 96-well plate (Maxisorp, Nunc) |
| Concentration of the Ag | 1 µg/ml |
| Buffer | PBS |
| Volume/well | 50 µl |
| Incubation | 1 night at ambient temperature |
| Washing: x1 | PBS - 0.05% (v/v) Tween 20 |
| Saturation | |
| Buffer | PBS-milk 2.5% (w/v) |
| Volume/well | 150 µl |
| Incubation | 1 h at 25° C. |
| Washing: x1 | PBS - 0.05% (v/v) Tween 20 |
| Antibody to be tested Supernatant of pure culture | |
| Volume/well | 50 µl |
| Incubation | 2 h at 25° C. |
| Washing: x3 | PBS - 0.05% (v/v) Tween 20 |
| Secondary antibody (conjugated peroxidase) | |
| Dilution | Anti-IgG and IgM (115-036-044, Jackson) 1/10,000 |
| Buffer | PBS-0.05% (v/v) Tween 20-0.5% (w/v) BSA |
| Volume/well | 50 µl |
| Incubation | 1 h at 25° C. |
| Washing: x3 | PBS - 0.05% (v/v) Tween 20 |
| Visualization | |
| Reagent | Tetramethylbenzidine (50-76-05, KPL, Inc.) |
| Volume/well | 50 µl |
| Incubation | 10 min |
| Stopping the reaction | $H_2SO_4$ 1M (S1526, Sigma) |
| Volume | 50 µl |

5—Isotyping of the Antibodies

The isotyping of the antibodies was determined using the SouthernBiotech SBA Clonotyping System/HRP kit (Cliniscience, Montrouge, France) as follows:

1. Coating of the plates
    Dilute the mouse anti-immunoglobulin antibody to a concentration of 5 µg/ml. Deposit 50 µl per well and incubate for 1 hour at 37° C. or 16 hours at ambient temperature.
2. Washing
    Rinse once with 200 µl/well of PBS-Tween20 0.05% (v/v).
3. Blocking
    Add 150 µl of PBS-Milk 2.5% (w/v) to each well and incubate for 1 hour at 37° C.
4. Washing
    Rinse once with PBS-Tween20 0.05% (v/v) buffer.
5. Preparation of the antibody samples to be tested
    Dilute the hybridoma culture supernatants to 1/10 with PBS-Tween20 0.05% (v/v)-BSA 0.5% (w/v). Deposit 50 µl per well and incubate for 2 hours at ambient temperature.
6. Washing
    Rinse 3 times with PBS-Tween20 0.05% (v/v) buffer.
7. Secondary antibody
    Deposit 50 µl per well of anti-mouse IgA, IgG1, IgG2a, IgG2b, IgG3 or IgM antibodies conjugated to peroxidase (HRP) (diluted to 1/2000 with PBS-Tween20 0.05% (v/v)-BSA 0.5% (w/v)) and incubate for 1 hour at ambient temperature.
8. Washing
    Rinse 3 times with PBS-Tween20 0.05% (v/v) buffer.
9. Reaction with the substrate
    Deposit 50 µl per well of Tetramethylbenzidine (KPL, Inc.) and incubate the plate for 10 minutes at ambient temperature.
10. Stopping the reaction
    Add 50 µl of $H_2SO_4$ to each well and read the absorbance at 450 nm, with the microplate reader (Dynex).

6—Results 5 hybridomas were stored: 17H10, 14A4, 4G6, 38E1, 40C10 for their excellent affinity for one of the peptides SEQ ID No. 7 to 11, as well as for the secreted domain of recombinant IRAP as indicated in FIGS. 1A-E.

Each of the antibodies 17H10, 14A4, 4G6, 38E1, 40C10 was tested by ELISA on plates in which 1 mg/mL of IRAP, or 2 mg/mL of IRAP tagged with a 6 His tag, was immobilized. The antibodies are incubated in the plates, and their detection is visualized using a secondary antibody coupled to peroxidase (HRP) recognizing the constant part of the monoclonal antibodies. The labelled IRAP-monoclonal antibody-antibody immune complex is visualized with TMB (3,3',5,5'-tetramethylbenzidine), a peroxidase chromogen substrate the colour of which turns blue in the presence of hydrogen peroxide and the colour of which becomes yellow in the presence of sulphuric acid (stopping the reaction). The reaction can be quantified by detection at 450 nm.

The results obtained show that the selected monoclonal antibodies can be used as antibodies for the detection of the secreted domain of IRAP using a sandwich ELISA. The dose-response curve indicates a detection limit of the secreted domain of IRAP from 1 to 100 ng/ml according to the antibody.

The clones were stored and cloned by producing limited dilutions in 96-well plates containing 10, 5, 3, 1 or 5 cells per well on average.

The products of the cloning were frozen in the following medium DMEM HT FCS 15% HCF 1% ATB (2): DMEM, 4 mM glutamine, HAT (hypoxantine 100 µM, thymidine 16 µM), 15% decomplemented foetal calf serum, 1% HEF (hybridoma enhancing supplement), 1% antibiotics (Penicillin/Streptomycin) completed with 10% DMSO (Dimethylsulphoxide)

Example 3

Assay of the IRAP Protein and/or One of its Isoforms and/or One of its Variants by an Immuno-Enzymatic Method in the Serum or the Plasma The IRAP protein and/or one of its isoforms sought in the serum or the plasma is bound by the specific antibody adsorbed on multi-well plates. The IRAP protein as well as its isoforms, even one or more of its variants which are bound are then visualized and quantified by measuring their enzymatic activity using L-leucine-paranitroanilide as substrate in the presence of 20 mM of L-methionine, the latter making it possible to avoid a cross reaction with possible contaminations by other aminopeptidases (Yamahara, N., Nomura, S., Suzuki, T., Itakura, A., Ito, M., Okamoto, T., Tsujimoto, M., Nakazato, H., and Mizutani, S. (2000) *Life Sci* 66(15), 1401-1410).

The enzymatic methods, and in particular using the L-leucine-paranitroanilide substrate make it possible to detect IRAP starting from a concentration of 10 µg/mL. An enrichment of IRAP by immunocapture reduces the detection threshold to 1 µg/mL. However these high detection thresholds are not very compatible with the detection of IRAP in the serum, Also, the use of very specific monoclonal antibodies to purify IRAP is indispensable, in order to reduce the detection threshold.

In order to validate the efficacy of the monoclonal antibodies, a sandwich ELISA was carried out using the antibodies 17H10 and 4G6.

The monoclonal antibody 17H10 is used as capture antibody at 15 µg/ml and the monoclonal antibody 4G6 is used as detection antibody. The 17H10-IRAP-4G6 complexes are visualized by an anti-isotype antibody directed against the mouse IgG2as conjugated to peroxidase (HRP), starting from samples of recombinant IRAP, or plasma from pregnant women (14-16 weeks) or men.

Figure 2:
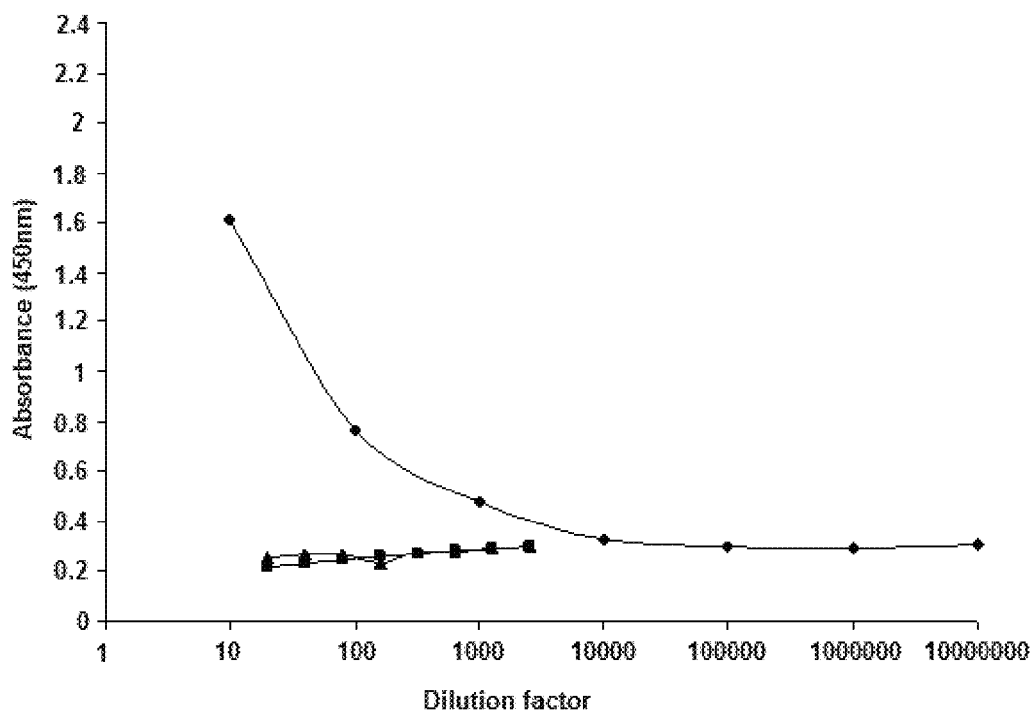
FIG. 2 represents the dose-response curve for the detection of IRAP in an ELISA where the monoclonal antibody 17H10 is used as capture antibody and the monoclonal antibody 4G6 as detection antibody. (♦) represents the assay of recombinant IRAP, (■) represents the assay of IRAP in serum from pregnant women, and (▲) represents the assay of IRAP in serum from men.

The results are shown in FIG. 2.

Under these conditions of use, the combination of antibodies 17H10-4G6—anti-IgG2a/HRP makes it possible to detect the secreted domain of the IRAP protein up to a concentration of 0.1 µg/ml.

This combination does not allow the detection of IRAP in these plasmas at the dilutions tested. The use of a fourth anti-HRP antibody conjugated to alkaline phosphatase makes it possible to increase the sensitivity up to 1 ng/ml.

Example 4

Assay of the IRAP Protein and/or One of its Isoforms and/or One of its Variants by an Immunohistochemical Method in Human Tissues The immunohistochemical assay was carried out using the avidin-biotin immunoperoxidase technique. Sections of human tissues taken beforehand, with a thickness of 4 µm were produced and stained using the streptavidin/biotin/peroxidase method.

The sections with their paraffin removed were placed in a 0.01 M citrate buffer and were treated three times for 5 min each at 90° C. and at 750 W in a microwave oven.

The sections were then incubated in hydrogen peroxide for 20 min and then incubated with serum from the animal host of the secondary antibody at 10% for 10 min in order to block the endogenous peroxidase activity and the binding to the non-specific immunoglobulins, respectively.

A monoclonal antibody of Example 2 at a dilution of 1:100 was added to the tissue sections and incubated for 1 h in a humid chamber at ambient temperature for the assay of IRAP and/or its isoforms and/or one of its variants.

The binding of the antibody was visualized by a biotinylated mouse anti-Ig antibody, followed by streptavidin conjugated to horseradish peroxidase.

The chromogenic development was carried out by immersion of the sections in 3-amino-9-ethylcarbazole.

The photographs were analyzed by counterstaining with Mayer's hematoxylin.

Example 5

Assay of the IRAP Protein and/or One of its Isoforms and/or One of its Variants for the Prognosis of Chemoresistance Chemoresistance is the consequence of the overexpression of IRAP. It can therefore be assayed according to Example 3 or 4 or by RIA or IRMA.

Example 6

Assay of the IRAP Protein and/or One of its Isoforms and/or One of its Variants for Measuring the Occurrence of Premature Labour The Concentration of IRAP Increases During Pregnancy.

It can therefore be predicted in the case of a decline in the circulating concentration of IRAP assayed according to Example 3 or 4 or by RIA or IRMA.

Example 7

Specificity of the Monoclonal Antibodies Directed Against the Extracellular Part of IRAP In order to validate the specificity of the antibodies of the invention, measurements of IRAP-antibody interaction were carried out in the presence of sera which had been diluted or not.

The antibody-IRAP interaction was measured as a function of the recombinant IRAP concentration, or of the recombinant IRAP diluted in serum from men or pregnant women diluted to $1/100^{th}$, by means of an ELISA sandwich using the antibodies 17H10 and 40C10.

Figure 3:
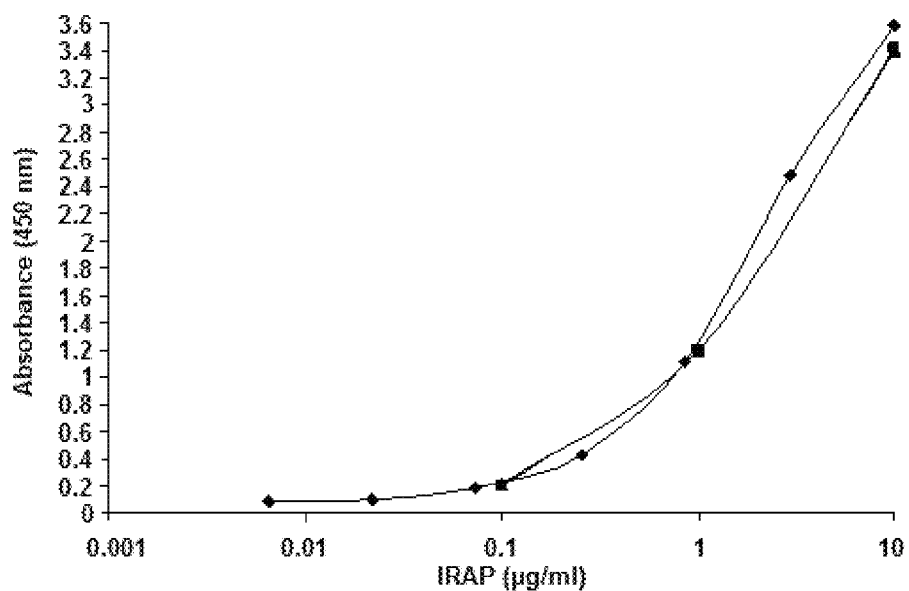
FIG. 3 represents the saturation dose curve for the detection of IRAP in an ELISA where the monoclonal antibody 17H10 is used as capture antibody and the monoclonal antibody 40C10 as detection antibody, (♦) represents the assay of recombinant IRAP, (■) represents the assay of recombinant IRAP diluted in serum from pregnant women, and (▲) represents the assay of recombinant IRAP diluted in serum from men.

The results are shown in FIG. 3.

These results show that IRAP is detectable at a concentration of 0.1 µg/mL in diluted serum, without there being interference with the other aminopeptidases contained in the serum.

These results show that the monoclonal antibodies are very specific to IRAP.

The invention claimed is:

1. A method for determining the concentration of circulating extracellular domain of the insulin-responsive aminopeptidase (IRAP) protein in the blood of a mammal subject, comprising conducting an in vitro immunoassay on a serum or plasma sample from said subject, utilizing an antibody that is selected from the group consisting of:
the monoclonal antibody secreted by the hybridoma deposited at the Collection Nationale de Culture de Microorganismes (CNCM) under accession number I-4181;
the monoclonal antibody secreted by the hybridoma deposited at the CNCM under accession number I-4182;
the monoclonal antibody secreted by the hybridoma deposited at the CNCM under accession number I-4183;
the monoclonal antibody secreted by the hybridoma deposited at the CNCM under accession number I-4184; and
the monoclonal antibody secreted by the hybridoma deposited at the CNCM under accession number I-4185.

2. The method according to claim 1, wherein the immunoassay utilizes two of said antibodies.

3. The method according to claim 2, wherein the immunoassay is a sandwich ELISA utilizing a capture antibody and a detection antibody.

4. The method according to claim 1, wherein the immunoassay can detect the circulating extracellular domain of the IRAP protein in the blood at a sensitivity of up to 1 ng/ml.

5. The method according to claim 1, wherein said IRAP protein comprises the amino acid sequence of SEQ ID NO: 1, SEQ ID NO: 2, SEQ ID NO: 3, SEQ ID NO: 4, SEQ ID NO: 5, or SEQ ID NO: 6.

* * * * *